United States Patent
Kamb et al.

(12) 
(10) Patent No.: US 6,566,057 B1
(45) Date of Patent: May 20, 2003

(54) METHODS AND COMPOSITIONS FOR PEPTIDE LIBRARIES DISPLAYED ON LIGHT-EMITTING SCAFFOLDS

(75) Inventors: Carl Alexander Kamb, Salt Lake City, UT (US); Majid Abedi, Salt Lake City, UT (US)

(73) Assignee: Deltagen Proteomics, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/269,006

(22) PCT Filed: Nov. 6, 1998

(86) PCT No.: PCT/US98/23778

§ 371 (c)(1),
(2), (4) Date: Mar. 17, 1999

(87) PCT Pub. No.: WO99/24617

PCT Pub. Date: May 20, 1999

Related U.S. Application Data

(63) Continuation of application No. 08/965,477, filed on Nov. 6, 1997, now Pat. No. 6,025,485, which is a continuation-in-part of application No. 08/812,994, filed on Mar. 4, 1997, now Pat. No. 5,955,275, which is a continuation-in-part of application No. 08/800,664, filed on Feb. 14, 1997.

(51) Int. Cl.[7] .......................... C12Q 1/68; C12N 15/00; C07K 1/00; C07H 21/02
(52) U.S. Cl. ..................... 435/6; 435/5; 435/320.1; 435/DIG. 22; 435/DIG. 24; 530/350; 536/23.1; 536/23.4
(58) Field of Search ..................... 435/6, 320.1, 69.1, 435/69.7, 4, DIG. 1, DIG. 22, DIG. 23, DIG. 24, 5; 530/350; 536/25.32, 23.4, 23.1, 18.1

(56) References Cited

U.S. PATENT DOCUMENTS

| 5,217,889 A | 6/1993 | Roninson et al. |
| 5,283,173 A | 2/1994 | Fields et al. |
| 5,364,783 A | 11/1994 | Ruley et al. |
| 5,491,084 A | 2/1996 | Chalfie et al. |

(List continued on next page.)

FOREIGN PATENT DOCUMENTS

| WO | WO93 10245 | 5/1993 |
| WO | WO 93 08701 | 5/1995 |

(List continued on next page.)

OTHER PUBLICATIONS

Alberts B., Bray D., et al. (Eds.), *Molecular Biology of the Cell*, Chapter 10, Control of Gene Expression, Second Edition, Garland Publishing, Inc., New York and London, (1989), pp. 551–599.

(List continued on next page.)

*Primary Examiner*—Padmashri Ponnaluri
(74) *Attorney, Agent, or Firm*—Bingham McCutchen LLP; Michael J. Shuster

(57) ABSTRACT

Methods and compositions for peptides or protein fragments displayed on scaffolds and libraries of sequences encoding peptides or protein fragments displayed on scaffolds that permit the properties of the library to be easily and quantitatively monitored are disclosed. The scaffold is a protein that is capable of emitting light. Thus, analysis of the expression of individual members of the library when they are expressed in cells may be carried but using instruments that can analyze the emitted light, such as a flow sorter (FACS), a spectrophotometer, a microtitre plate reader, a CCD, a fluorescence microscope, or other similar device. This permits screening of the expression library in host cells on a cell-by-cell basis, and enrichment of the library for sequences that have predetermined characteristics.

42 Claims, 9 Drawing Sheets

U.S. PATENT DOCUMENTS

| | | | |
|---|---|---|---|
| 5,569,588 | A | 10/1996 | Ashby et al. |
| 5,683,888 | A | 11/1997 | Campbell |
| 5,741,668 | A | 4/1998 | Ward et al. |

FOREIGN PATENT DOCUMENTS

| | | |
|---|---|---|
| WO | WO95/19988 | 9/1995 |
| WO | WO97/20078 | 6/1997 |
| WO | 97/14514 | 8/1997 |
| WO | WO97/48820 | 12/1997 |
| WO | WO98/07886 | 2/1998 |
| WO | WO95/16694 | 6/1998 |

OTHER PUBLICATIONS

Anderson M.T., Tjioe I.M., Lorincz M.C., Parks D.R., Herzenberg L.A., Nolan G.P., Herzenberg, "Simultaneous Fluorescence–Activated Cell Sorter Analysis of Two Distinct Transcriptional Elements Within a Single Cell Using Engineered Green Fluorescent Proteins,", L.A., *Proc. Natl. Acad. Sci.* (*USA*) 93: 16, 8508–8511 (1996).

Baillie, Rebecca A., et al., "Transient transfection of chick–embryo hepatocytes," J Nutr. Bioechem 4:431–439 (Jul. 1993).

Bellen H.J., O'Kane C.J., et al., "P–element–mediated Enhancer Detection: A Versatile Method to Study Development in Drosophila," *Genes Dev.* 3: 1288–1300 (1989).

Chalfie M., Tu Y, et al., "Green Fluorescent Protein as a Marker for Gene Expression," *Science* Feb. 11; 263 : 802–805 (1994).

Clontech 96/97 Catalog: Innovative Tools to Accelerate Discovery, pp. 91–99.

Clontech Catalog 97/98 pp. 111–118.

Clontech Catalog 98/99 pp. 151–162.

Cormack B.P., Valdivia R.H., and Falkow S., "FACS–Optimized Mutants of the Green Fluorescent Protein (GFP)," *Gene* 173: 33–38 (1996).

Cornwell, Richard D., et al., "Description of the leukocyte function–associated antigen 1 (LFA–1 or CD11a) promoter, "Proceedings of the National Academy of Sciences of the United States of America, 90:4221–4225 (May 1993).

Dorsky, David I., et al., "Detection of HIV–1 Infection with a Green Fluorescent Protein Reporter System", Journal of Acquired Immune Deficiency Syndromes and Human Retrovirology, Lippincott–Raven Publishers, Philadelphia, vol. 13, pp. 308–313 (1996).

Duchange N., Ochoa A., et al., Identification of an Enhancer Involved in the Melanoma–specific Expression of the Tumor Antigen Melanotransferrin Gene, *Nucleic Acids Res.* 20: 2853–2859 (1992).

Fieck A., Wyborski D.L., and Short J.M., "*Modifications of the E.Coli* Lac Repressor for Expression in Eukaryotic cells: Effects of Nuclear Signal Sequences on Protein Activity and Nuclear Accumulation," *Nucleic Acids Res.* 20: 1785 (1992).

Fuse N., Yasumoto K., et al., Identification of a Melanocyte–Type Promoter of the Microphthalmia–Associated Transcription Factor Gene, *Biochem. Biophys. Res. Commun.* 219: 702–707 (1996).

Gervaix, Alain, et al., "A New Reporter Cell Line to Monitor HIV Infection and Drug Susceptibility in vitro," Proc. National Academy of Science, vol. 94, pp. 4653–4658 (Apr. 1997).

Hagen D.C., McCaffrey G., Sprague G.F. Jr., "Pheromone Response Elements Are Necessary and Sufficient for Basal and Pheromone–Induced Transcription of the FUS1 Gene of *Saccharomyces cerevisae*," *Mol. Cell Biol.* 11: 6, 2952–61 (1991).

Hanahan D., "Heritable Formation of Pancreatic β–Cell Tumours in Transgenic Mice Expressing Recombinant Insulin/Simian Virus 40 Oncogenes," *Nature* May 11; 20:2233–2239 (1985).

Harrison R. W., and Miller J.C., "Functional Identification of Genes Up– and Down–Regulated by Glucocorticoids in AtT–20 Pituitary Cells Using an Enhancer Trap," *Endocrinology* Jul.; 137:2758–2765 (1996).

Herskowitz I., "Functional Inactivation of Genes by Dominant Negative Mutations," *Nature* 329: 219–222 (1987).

International Search Report, PCT/US98/04376, mailed Feb. 27.

International Search Report, PCT/US98/02758, mailed Jul. 20, 1998.

International Search Report,PCT/US98/23778, mailed Feb. 6, 1999.

Iida A., Chen S.T., et al., "Inducible Gene Expression by Retrovirus–Mediated Transfer of a Modified Tetracycline––Regulated System," *J. Virol* 70: 6054–6059(1996).

Kavathes P., Sukhatme V.P., et al., Isolation of the Gene Encoding the Human T–lymphocyte Differentiation Antigen Leu–2 (T8) BY Gene Transfer and Cdna Subtraction, *Proc. Natl. Acad. Sci.* (*USA*) 81: 7688–7692 (1984).

Koh J., Enders G.H., et al., "Tumour–Derived p16 Alleles Encoding Proteins Defective in Cell–Cycle Inhibition," *Nature* 375: 506–510 (1995).

Kozak M., "Point Mutations Define a Sequence Flanking the AUG Initiator Codon That Modulates Translation by Eukaryotic Ribosomes," *Cell* Jan. 31; 44: 283–292 (1986).

Lewin B, *Gene V*, Chapter 29, Building the Transcription Complex: Promoters, Factors, and RNA Polymerases, Oxford University Press, Oxfrod, U.K. (1994), pp. 847–877.

Martin, Franck, et al., "The affinity–selection of a minibody polypeptide inhibitor of human interleukin–6," *The EMBO Journal*, 13(22) pp. 5303–5309, 1594.

Myers R.M., Tilly K, and Maniatis T., "Fine Structure Genetic Analysis of a β–Globin Promoter," *Science* 232: 613–618 (1986).

Pessi, A., et al. "A designed metal–binding protein with a novel fold,", *Nature*, 362 367–369, Mar. 25, 1993.

Qin Z., Kruger–Krasagakes S., et al., "Expression of Tumor Necrosis Factor by Different Tumor Cell Lines Results Either in Tumor Suppression or Augmented Metastasis," *Exp. Med.* 178: 355–360.

Ross J., "mRNA Stability in Mammalian Cells," *Microbiol. Rev.*: 423–450 (1995).

Serrano M., Hannon G.J., et al., "A New Regulatory Motif in Cell–Cycle Control Causing Specific Inhibition of Cyclin D/CDk4," *Nature* 366, 704–707 (1993).

Shibata K., Muraosa Y., et al., "Identification of a cis–Acting Element that Enhances the Pigment Cell–specific Expression of the Human Tyrosinase Gene," *J. Biol. Chem.* 267: 20584–20588 (1992).

Simmons D., and Seed B. "Isolation of a cDNA Encoding CD33, a Differentiation Antigen of Myeloid Progenitor Cells," *J Immunol* 141: 2797–2800 (1988).

Valdivia, Raphael H. and Falkow, Stanley, "Bacterial Genetics By Flow Cytometry: Rapid Isolation Of *Salmonella typhimurium* Acid–inducible Promoters By Differential Fluorescence Induction," 1996 *Blackwell Science Ltd., Molecular Microbiology*, 22(2), pp. 367–378.

Wasylyk B., Wasylyk C., and Chambon P., "Short and Long Range Activation by the SV 40 Enhancer," *Nucleic Acids Res.* Jul. 25; 12: 5589–5608 (1984).

Wilkinson G. W., and Akrigg A., "Constitutive and Enhanced Expression from the CMB Major E Promoter in a Defective Adenovirus Vector," *Nucleic Acids Res.* May 11; 20: 2233–239 (1992).

Yokoyama K., Yasumoto K., et al., "Cloning of the Human DOPAchrome Tautomerase/Tyrosinase–related Protein 2 Gene and Identification of Two Regulatory Regions Required for its Pigment Cell–specific Expression," *J. Biol. Chem.* 269: 27080–27087 (1994).

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence:
      hypothetical sequence for illustrative purposes

<400> SEQUENCE: 1
acggtgcata c                                                       11
```

METHODS AND COMPOSITIONS FOR PEPTIDE LIBRARIES DISPLAYED ON LIGHT-EMITTING SCAFFOLDS

RELATED APPLICATION DATA

This application is a section 371 application of PCT/US98/23778, filed Nov. 6, 1998, which application claims priority and is a continuation to Ser. No. 08/965,477, filed Nov. 6, 1997, now U.S. Pat. No. 6,025,485, which is a continuation-in-part of Ser. No. 08/812,994, filed Mar. 4, 1997, now U.S. Pat. No. 5,955,275, which is a continuation-in-part of Ser. No. 08/800,664, filed Feb. 14, 1997, pending.

FIELD OF THE INVENTION

The present invention relates to the field of molecular biology, and more particularly to genetic sequences encoding peptide display scaffolds capable of emitting light, and to peptide display libraries based on these scaffolds.

BACKGROUND

Proteins can bind to numerous chemical species, or ligands, including small organic molecules, nucleic acids, peptides, metal ions, and other proteins. Indeed, to carry out a biological function, a protein must interact with another entity. The capacity of amino acid polymers to participate in chemical interactions is one of the major reasons for their ascendancy in the biological world. Much as the AND gate is the basic component of binary computers, individual proteins and their cognate ligands are the fundamental mechanism upon which cells and organisms are built.

One of the most significant areas of research and development in the pharmaceutical industry involves methods to better design or screen for ligands that interact specifically with defined protein targets. Discovery of such ligands is the engine that drives development of new pharmaceutical compounds. Typically, efforts to find ligands focus on small molecules, antibodies, peptides, or RNA and DNA aptamers. Depending on the particular application, such ligands may provide lead compounds for drug development or probes for further research into biological processes.

A flurry of recent experiments has explored the utility of peptide binding assays for discovery of peptide-based ligands that bind specific protein targets in vitro. One of the most popular methods involves phage display, i.e., the presentation of peptide sequences on the surface of phage particles (Cwirla S. E., Peters E. A., et al. *Proc Natl Sci USA* August 1990; 87(16):6378–6482 and Cortese R., Monaci P., et al. *Curr Opin Biotechnol* December 1996; 7(6):616–621). Filamentous phage such as M13 and f1 have been engineered to express and present foreign peptide sequences. Two different approaches have been of primary interest; both involve incorporation during phage particle assembly of chimeric coat proteins that include segments of foreign sequence. The first involves the phage coat protein gp3 which is normally present on the phage coat in only a few copies per virus. Sequences that might be toxic at higher concentration on the viral coat, including relatively large protein domains, can be presented effectively using gp3 fusions. The second approach involves gp8, which is the major coat protein present in thousands of copies per virus. gp8 fusions have the advantage that they may reside on the virus in large amounts, thus increasing the avidity of the interaction between the virus and potential receptors. But as a consequence of this increased amount of fusion protein, the virus is more selective about which sequences can be displayed using gp8 (Makowski, L. *Gene* Jun. 15, 1993; 128(1):5–11).

Other modes of surface display have also been considered. Larger, more complex viruses including lambda and T4 have been exploited for surface display (Mikawa Y. G., Maruyama I. N. et al. *J Mol Biol* Sep. 13, 1996; 262(1):21–30 and Efimov V. P., Nepluev I. V., et al. *Virus Genes* 1995; 10(2):173–177). The basic approach is similar to that used for filamentous phages; that is, viruses are assembled in bacterial host cells which incorporate chimeric coat or tail fiber proteins that bear the foreign sequences. In contrast to filamentous phages, however, these viruses assemble completely inside the cytoplasm and are released through cell lysis; thus, coat proteins are cytoplasmic proteins as opposed to membrane proteins, a feature that may increase the flexibility of the display mechanism.

Bacterial cells have also been examined as vehicles for surface display. The general approach is to use a membrane protein (e.g., OmpA in *E. coli*) to display protein or peptide epitopes in an accessible manner on the cell surface (Georgiou G., Stephens D. L., et al. *Protein Eng* February 1996; 9(2):239–247). Even mammalian cells have been employed as vehicles for surface display. For example, membrane proteins such as CD4 and CD8 were first cloned by expression and ligand-based selection in mammalian cells. (Maddon P. J., Littman D. R., et al. *Cell* August 1985; 42(1):92–104 and Littman D. R., Thomas Y., et al. *Cell* February 1985; 40(2):237–246).

One of the most appealing aspects of surface or phage display is the ability to screen complex peptide libraries for rare sequences that bind selectively to defined protein targets. The combinatorial chemistry required to generate a diverse population of peptides involves oligonucleotide synthesis. Furthermore, twenty amino acids with their wide spectrum of chemical properties (e.g., hydrophobicity, charge, acidity, and size) can create substantial chemical complexity, more so than, for example, nucleotides. However, like nucleotides, peptide libraries displayed on phage can be reproduced with relative ease. The replication requires nucleic acid intermediates, but the advantages of amplification are the same; namely, the capacity for biochemical enrichment without substantial loss of starting material, and the ability to perform genetic experiments.

Although surface display of peptides or proteins is useful for selecting ligands in vitro; it is less appropriate for selections that involve intracellular processes. For this application, expression systems inside the cell must be employed. Intracellular ectopic expression of antibody libraries is one mode of expression (Sawyer C., Embleton J., et al. *J Immunol Methods* May 26, 1997; 204(2):193–203); a second involves expression of peptide libraries generated as fusions to cytoplasmic proteins such as thioredoxin and GAL4 from yeast (Colas P., Cohen B., et al. *Nature* Apr. 11, 1996; 380(6574):548–550 and Fields S., Song O. *Nature* Jul. 20, 1989; 340(6230):245–246).

Although for certain applications (e.g., construction of an interaction or proteome map), proteins or relatively large protein fragments are superior to peptides for display, for other applications, it is advantageous not to be constrained by natural protein sequences. To identify or devise novel proteinacious ligands and/or inhibitors of specific targets, it may be simpler to generate and examine a chemically diverse library of relatively low molecular weight compounds based on peptides. In addition, peptide libraries can be used in genetic selections and screens to pinpoint peptide ligands that bind important intracellular targets, similar to selections employed in, e.g., the yeast two-hybrid system (Fields S., Song O. *Nature* Jul. 20, 1989; 340(6230):245–246).

Though a potentially powerful tool, intracellular display of peptide libraries by the methods mentioned above suffers from several limitations. First, it is often difficult to know what the expression level of specific peptides or peptide fusions is; in many cases, even an average measure of expression level is difficult to obtain. Second, the diversity of the library is not easily estimated. It may be, for example, that only a small subset of possible peptide sequences are presented efficiently by a particular expression system. Third, it is not always easy to follow the expression of peptides in particular cells; for example, to know whether or not a specific cell is expressing a member of the library. Fourth, it is not generally possible to manipulate the library to alter its average properties once the library has been generated; for example, to isolate library sequences compatible with high expression. Fifth, efforts to restrict conformational freedom (in order to promote higher binding energies), e.g., by inserting the peptides into the interior of protein sequences may compound the problems discussed above. Such inserted libraries are likely to perturb the function and stability of the fusion partners in ways difficult to predict and measure. A method is therefore needed to overcome these limitations associated with peptide or protein fragment display libraries.

SUMMARY

The present invention overcomes the above-mentioned limitations by providing methods and compositions for peptides or protein fragments displayed on scaffolds and libraries of sequences encoding peptides or protein fragments displayed on scaffolds that permit the properties of the library to be easily and quantitatively monitored. The scaffold is a protein that is capable of emitting light. Thus, analysis of the expression of individual members of the library when they are expressed in cells may be carried out using instruments that can analyze the emitted light, such as a flow sorter (FACS), a spectrophotometer, a microtitre plate reader, a CCD, a fluorescence microscope, or other similar device. This permits screening of the expression library in host cells on a cell-by-cell basis, and enrichment of the library for sequences that have predetermined characteristics.

A genetic sequence encoding a peptide display scaffold is used to create the libraries of the present invention. This scaffold sequence comprises a first sequence that encodes a molecule capable of emitting light. The first sequence contains a site, the location of which allows a second sequence to be inserted at the site while maintaining the ability of the molecule encoded by the first and second sequences to emit light.

These and other features, aspects, and advantages of the present invention will become better understood with regard to the following description, appended claims, and accompanying drawings.

DETAILED DESCRIPTION OF PREFERRED EMBODIMENTS

Definitions

Figure 1:
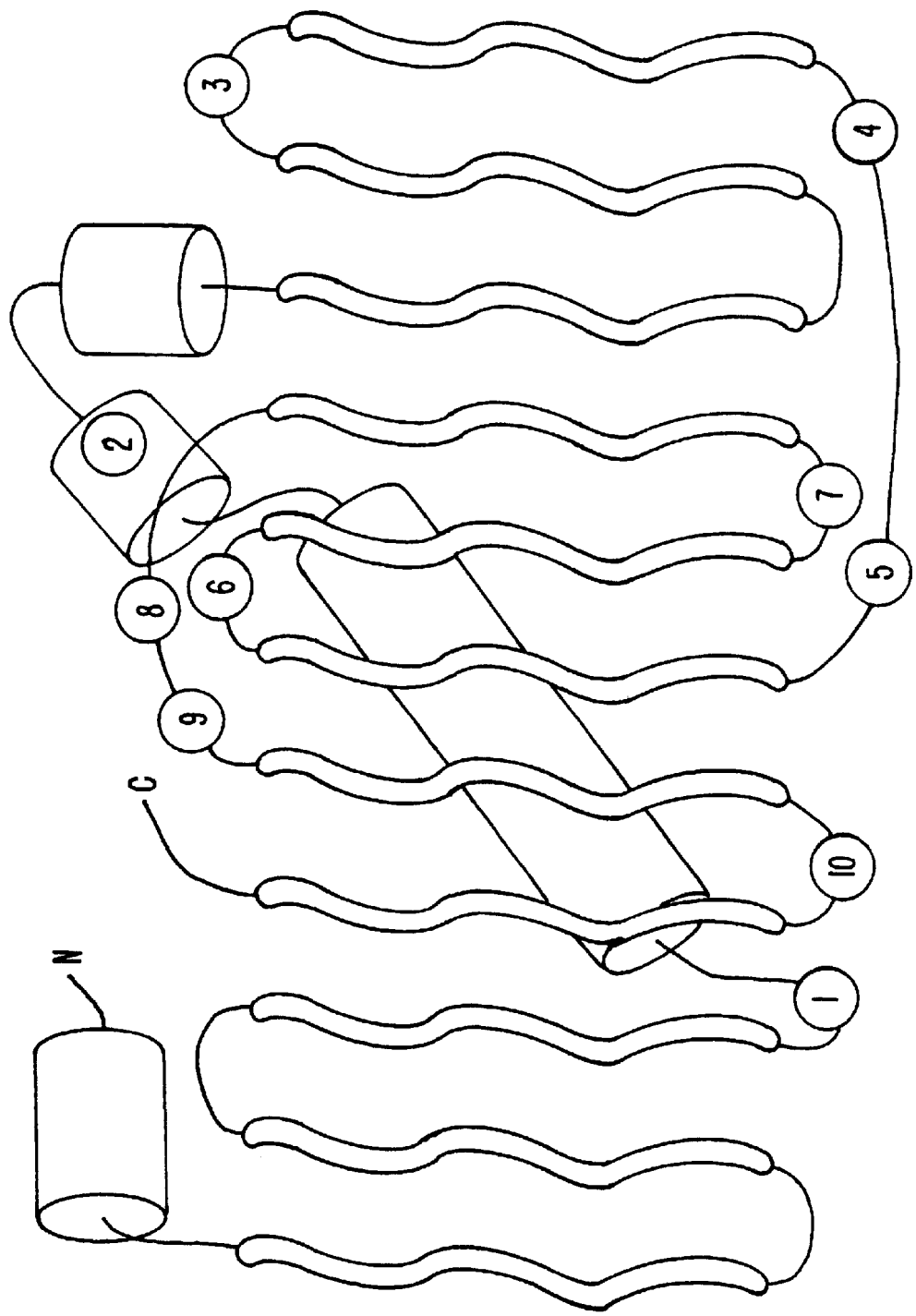
FIG. 1: Model of the backbone of GFP showing sites of aptamer insertion. Numbers 1–10 correspond to insertion sites in pVT22–pVT31, respectively.

The term "scaffold" refers to a protein that can be used to display amino acid sequences as part of a fusion protein or insertion involving the scaffold as a backbone.

The term "protein domain" or "protein fragment" refers to a portion of a native protein typically generated by expression of gene or cDNA fragments.

The term "aptamer" refers to a polymeric molecule, typically composed of nucleotides or amino acids, capable of adopting specific conformations and interacting physically and/or chemically with other molecules.

The term "FU" is fluorescence units. Note FU are arbitrary measures of fluorescence and cannot be compared between experiments.

The terms "genetic library" or "library" refer to a collection of DNA fragments that may range in size from a few base pairs to a million base pairs. These fragments are contained as inserts in vectors capable of propagating in host cells that may be bacterial, archaebacterial, fungal, mammalian, insect, or plant cells.

The term "insert" in the context of a library refers to an individual DNA fragment that constitutes a single member or element of the library.

The term "sub-library" refers to a portion of a genetic library that has been isolated or selected by application of a specific screening or selection procedure.

The term "vector" refers to a DNA or RNA sequence that is capable of propagating in particular host cells and can accommodate inserts of foreign nucleic acid. Typically, vectors can be manipulated in vitro to insert foreign nucleic acids and the vectors can be introduced into host cells such that the inserted nucleic acid is transiently or stably present in the host cells.

The term "host cell" refers to a cell of prokaryotic, archaebacterial, or eukaryotic origin that can serve as a recipient for a vector that is introduced by any one of several procedures. The host cell often allows replication and segregation of the vector that resides within. In certain cases, however, replication and/or segregation are irrelevant; expression of vector or insert DNA is the objective. Typical bacterial host cells include *E. coli* and *B. subtilis*; archaebacterial host cells include *S. acidocaldarius* and *H. salinarium*; fungal host cells include *S. cerevisiae* and *S. pombe*; plant cells include those isolated from *A. thaliana*, and *Z.*

*maize*; insect host cells include those isolated from *D. melanogastor, A. aegypti*, and *S. frugiperda*; and mammalian cells include those isolated from human tissues and cancers including melanocyte (melanoma), colon (carcinoma), prostate (carcinoma), and brain (glioma, neuroblastoma, astrocytoma).

The term "reporter" refers to a protein (and "reporter gene" to the gene that encodes it) that serves as a surrogate for expression of specific sequences in the genome, or that allows the activity of cis regulatory sequences to be monitored easily and, preferably, in a quantitative fashion. Reporters may be proteins capable of emitting light such as GFP (Chalfie M., Tu Y., et al., *Science* Feb. 11, 1994; 263:802–805) or luciferase (Gould S. J., and Subramani S., *Anal, Biochem.* November 15; 175: 5–13 (1988)), or intracellular or cell surface proteins detectable by antibodies such as CD20 (Koh J., Enders G. H., et al., *Nature* 1995 375:506–510). Alternatively, reporter genes can confer antibiotic resistance such as hygromycin or neomycin resistance (Santerre R. F., et al., *Gene* 30: 147–156 (1984)).

The terms "bright" and "dim" in the context of a cell sorter refer to the intensity levels of fluorescence (or other modes of light emission) exhibited by particular cells. Bright cells have high intensity emission relative to the bulk population of cells; dim cells have low intensity emission relative to the bulk population.

The term "perturbagen" refers to an agent that acts in a transdominant mode to interfere with specific biochemical processes in cells. In the context of the present invention, perturbagens are typically either proteins, protein fragments, or peptides, although the term also encompasses nucleic acids and other organic molecules with similar properties.

The term "transdominant" describes a type of interaction whereby the agent (most typically a perturbagen) is a diffusable substance that can bind its target in solution. Thus, a transdominant agent is dominant as opposed to recessive in a genetic sense, because it acts on gene products and not on alleles of genes. The effects of a perturbagen are visible in the presence of wild type alleles of its target.

The term "phenocopy" refers to a phenotypic state or appearance that mimics or resembles the state induced by mutation of a specific gene or genes. This state may, for example, be induced by expression of perturbagens within a particular host cell.

The term "GFP" refers to a member of a family of naturally occurring fluorescent proteins, whose fluorescence is primarily in the green region of the spectrum. The term includes mutant forms of the protein with altered spectral properties. Some of these mutant forms are described in Cormack B. P., Valdivia R. H., and Falkow S., *Gene* 173: 33–38 (1996) and Ormo M., Crystal structure of the *Aequorea victoria* green fluorescent protein, *Science* 273 (5280): 1392–1395 (1996). The term also includes polypeptide analogs, fragments or derivatives of polypeptides which differ from naturally-occurring forms by the identity or location of one or more amino acid residues, for example, deletion, substitution and addition analogs, which share some or all of the properties of the naturally occurring forms. Wild type GFP absorbs maximally at 395 nm and emits at 509 nm. High levels of GFP expression have been obtained in cells ranging from yeast to human cells. It is a robust, all-purpose reporter, whose expression in the cytoplasm can be measured quantitatively using instruments such as the FACS. The term also includes BFP, the coding sequence for which is described in Anderson M. T., Tjioe I. M., Lorincz M. C., Parks D. R., Herzenberg L. A., Nolan G. P., Herzenberg L. A., *Proc. Natl Acad. Sci. (USA)* 93: 16, 8508–8511 (1996).

The term "constrained conformation" when used in reference to an amino acid sequence means a position in which the sequence is tethered at both ends (for example, to a protein) imposing significant restraints on the conformational flexibility of the amino acid sequence. Limiting the conformational flexibility of the amino acid sequence promotes higher binding energies between the sequence and potential binding partners increasing the efficiency of screening methods.

A. Overview

The present invention provides methods and compositions for constructing and using peptides or protein fragments displayed on scaffolds and libraries of sequences encoding peptides or protein fragments displayed on scaffolds. The methods employ as a scaffold a protein capable of emitting light. This permits manipulation and rigorous, quantitative analysis of the library, advantages that are either difficult or impossible to obtain in other settings. In a preferred embodiment, the scaffold used is an autofluorescent protein, e.g., the green fluorescent protein (GFP) from the jellyfish *Aequorea Victoria* (Chalfie M., Tu Y., et al. *Science* Feb. 11, 1994; 263(5148):802–805).

Sites on the scaffold protein that are appropriate for insertion of random peptide sequences are identified. Appropriate sites would accommodate peptide insertions without seriously disturbing protein function. Sites that not only accept small inserted sequences, but also accept a wide variety of different sequences are described. Such sites are by definition robust to chemical perturbation. Some proteins accommodate insertions at numerous sites throughout their primary sequence. Others are much less accommodating. It is difficult in general to predict which proteins are robust to insertions, and which sites in a particular protein are best suited to insertion of multiple independent sequences. However, in cases where three-dimensional structures are available, or where primary sequences of several members of a protein family can be examined, certain regions are more likely to accept insertions. Such regions include solvent exposed regions and regions of relatively high primary sequence variability.

Autofluorescent proteins provide a ready assay for identification of appropriate insertion locations. Because the activity of the protein (and by inference its expression level) can be monitored quantitatively using a flow sorter, it is simple to assay many independent insertions either sequentially or in bulk population. The best candidates can then be screened for or selected from the population. Mutant proteins are generated by manipulating the DNA sequence, such that a variety of different insertions are generated and examined by flow cytometry to locate variants that retain autofluorescent properties. Variants identified in this fashion reveal the nature of sites within the protein best suited for display of foreign sequence.

Once suitable insertion sites are discovered, it is possible to monitor quantitatively the characteristics (light emission in the case of an autofluorescent protein) of the individual scaffolds that are chosen. The flow sorter serves as an appropriate tool for such analysis. A family of peptides, preferably a relatively large family (e.g., having from around $10^3$ to $10^7$ members) is inserted into the scaffolds at the predetermined position to generate an expression library, and the fluorescence properties of the library are examined. Quantitative parameters such as mean fluorescence intensity and variance can be determined from the fluorescence intensity profile of the library population (Shapiro H. *Prac-* tical *Flow Cytometry* 1995 217–228). This permits an estimate of the percentage of library sequences that do not lend themselves to expression in this context, and hence, an estimate of the library complexity.

The flow sorter can be used not only as a screen to examine the properties of the generated expression libraries, but also as a tool to manipulate and bias the libraries in potentially useful ways. For example, in certain cases it may be helpful to select from the expression library those sequences that express the highest levels of protein in cells. Alternatively, it may be desirable simply to exclude all library constructs that do not express scaffold levels above the background; many of these negative or "dim" cells may harbor expression constructs that produce truncated or misfolded proteins that are degraded or do not function as soluble peptide display scaffolds (Dopf J., Horiagon T. M. *Gene* 1996 173:39–44). The flow sorter permits such selections to be carried out with extraordinary efficiency because cells can be sorted at a rate of ten to one hundred million per hour (Shapiro H. *Practical Flow Cytometry* 1995 217–228).

The libraries of sequences encoding peptides displayed on autofluorescent scaffolds of the present invention provide the means to carry out genetic or pseudogenetic experiments of considerable interest. These experiments involve generation of phenocopies of mutants by overexpression of peptide inhibitors in cells. Such experiments have been performed in specific contexts before (PCT US97 145 14, Selection Systems for the Identification of Genes Based on Functional Analysis;

U.S. patent application Ser. No. 08/812,994, Methods for Identifying Nucleic Acid Sequences Encoding Agents that Affect Cellular Phenotypes, filed Mar. 4, 1997).

Peptide-based ligands are useful in a variety of contexts as probes of biological functions, or as aids in the development of therapeutic compounds. A variety of techniques have been developed to isolate specific peptides from complex libraries which bind to defined targets in vitro. In addition, the notion of using peptide libraries expressed in cells as agents to disrupt specific biochemical pathways has been explored recently (PCT US97 145 14, Selection Systems for the Identification of Genes Based on Functional Analysis). These agents are called "perturbagens" by analogy with mutagens that alter the genetic material. Perturbagens, rather than causing mutations in genes, achieve their effect by specifically binding targets in the cell, thereby perturbing particular biochemical processes.

To enable such pseudo-genetic analysis, a display system that operates inside living cells is required. The protein scaffolds of the present invention provide such a display system. The protein scaffolds of the present invention are relatively resistant to degradation by proteases within the cell and display peptides in a constrained conformation. In addition, they are soluble—even when joined to a wide variety of foreign peptide sequences. They also allow the quantitative performance of the scaffold to be measured in terms of its ability to display peptides and maintain high levels of stability and expression in cells.

B. Insertion Site Design

An initial step in designing the display scaffold is determining the site (or sites) that accommodate foreign peptide sequences. In the case of GFP, it is likely that the molecule is highly sensitive to perturbations as dramatic as amino acid insertions due to the compact, spare nature of the structure (Ormo M., Cubitt A. B., et al. *Science* 1996 273:1392–1395). The recently-solved crystal structure of GFP reveals that this protein assumes a beta-barrel structure and has ten solvent-accessible loops, two of which connect the helical chromophore segment to the rest of the protein (Ormo M., Cubitt A. B. et al. *Science* 1996 273:1392–1395). The remaining 8 loops connect the beta-strands of the barrel to one another. These loops are candidate sites for the insertion of random aptamers. By inserting aptamers into the beta-turns in GFP, loops can be identified by flow cytometry which accommodate random aptamers while allowing GFP to retain fluorescence. Although GFP is known to readily accept N- and C-terminal fusions, there are two reasons for preferring internal sites for peptide display. First, conformational freedom is reduced by tethering the two ends of the aptamer to rigid components of the structure; for aptamers located at the protein termini, it is only possible to tether one end (Ladner, R. *Trends Biotechnol* 1995 13:426–430). Second, aptamers at either terminus will be charged, which limits the range of chemical/structural possibilities encompassed by the library.

In the case of other autofluorescent proteins for which three-dimensional structural information is not available, it may be possible to exploit comparisons of gene family members. One historical approach to establishing the structural requirements of proteins is to compare amino acid sequences of proteins of similar function, within a single species and among different phyla. Such comparisons may shed light on the structurally important regions because these are the most likely to be conserved among family members. Sites that tolerate amino acid changes without compromising protein function are the most likely to vary in sequence.

An additional approach that is possible with autofluorescent proteins involves a blind "hit or miss" approach. The sequence of an autofluorescent protein may be deliberately varied such that, e.g., an insertion at every possible position is generated (Ausubel F. M., Brent R., et al., *Current Protocols in Molecular Biology*, John Wiley and Sons, New York (1996), Sambrook J., Fritsch E. F., and Maniatis, T., *Molecular Cloning*: A Laboratory Manual, Second Edition, CHSL Press, New York (1989)). These insertion mutants may be analyzed individually using a flow sorter after expression in cells, or the entire population may be analyzed in bulk, and the mutants hat produce fluorescent protein at or above a predetermined threshold level in cells ay be collected, separated from each other, and analyzed individually afterward.

C. Genetic Libraries

Once suitable scaffold candidates have been identified by the experiments described above, the candidates must be tested further to define the individual scaffolds that are capable of displaying a wide range of peptide sequences at the specified site(s). It is possible, for instance, that a site defined by experiments described above may only accept a very limited diversity of inserted sequences; alternatively, it is possible that the linker inserted above may represent an upper limit for the size of inserted sequences. Thus, introduction of an additional insert from the library may render the protein, e.g., unstable. Therefore, the capacity of the scaffold candidates to accept library inserts must be tested by introduction of a population of different inserts, and quantitation of the effects of the library sequences on the level of scaffold expression.

The library may be generated in a variety of ways. The simplest way to create a large number of diverse sequences involves oligonucleotide synthesis. For example, a random oligonucleotide of length 24 encodes all possible peptides of length 8, a number that exceeds ten billion. A library of this size is so large that it is difficult to prepare. Libraries typically range in size from at least several thousand to about one hundred million individual species. Such libraries might involve all possible peptides of length 6, or might involve subsets of libraries composed of longer sequences.

Libraries may also be generated from natural DNA sequences such as mRNA or genomic DNA. Typically such libraries would be biased toward native proteins and protein fragments. Thus, these libraries may contain a significant fraction of sequences that encode polypeptides that interact with native proteins in the cell. When such fragments are inserted into the autofluorescent scaffold, they may fold into a conformation that resembles a domain from the cognate native protein from which they are derived (Bartel P. L., Roecklein J. A., et al. *Nat Genet* January 1996; 12(1):72–77).

DNA sequences generated as synthetic oligonucleotides or as cDNA or genomic DNA can be inserted into appropriate expression vectors in a variety of ways. Such methods for vector and insert preparation, ligation, and transformation are known in the art (Ausubel et al., supra). In general, it is necessary to produce a vector that has an appropriate restriction site for inserting foreign DNA into the scaffold gene, to produce a linear vector such that the site is available for ligation, to mix the vector and library insert DNAs together under suitable reaction conditions, to permit the ligation to proceed for sufficient time, and to introduce the ligated material into a suitable host such as, e.g., *E. coli* such that individual clones (preferably a few million) can be selected for further experiments.

D. Expression Vector

The invention preferably employs an expression vector capable of producing high levels of the peptide or protein fragment displayed on a scaffold protein. As discussed above, it is often difficult to determine the quality (i.e., diversity and expression levels) inside cells of a library of sequences encoding a peptide/scaffold combination. In the case of autofluorescent proteins, however, it is relatively easy to determine the quantitative characteristics of the library. A flow sorter or similar device provides rapid quantitative information about the expression level of the library within living cells (Shapiro H. *Practical Flow Cytometry* 1995).

The choice of promoter used to drive expression of the autofluorescent scaffold protein depends on which cells are to be examined. In most organisms and cell types that are used in biological or medical experiments, numerous promoter types are available. In general, strong promoters are preferred, because they will facilitate higher expression levels of library sequences in the chosen host cells. Such promoters are typically derived from housekeeping genes that are expressed at high levels in most or all cell types in the organism, or from viruses. Numerous such cis regulatory sequences are known in the art, suitable for driving expression in mammalian cells, insect cells, plant cells, fungi or bacteria (Ausubel et al., 1996). For example, in eukaryotes the promoter for beta actin is useful (Qin Z., Kruger-Krasagakes S., et al. *J. Exp. Med.* 178:355–360); in plants the Cauliflower Mosaic Virus 35S promoter(Goddijn O. J., Pennings E. J., et al., *Transgenic Res.* 1995 4:315–323). In mammalian cells, the cytomegalovirus (CMV) promoter is commonly used; and in general, a promoter that drives high level expression of, e.g., a housekeeping or viral gene can be identified with Telative ease using current molecular genetic methods.

E. Nucleic Acid Transfer

During the last two decades several basic methods have evolved for transferring exogenous nucleic acid into host cells. These methods are well-known in the art (Ausubel F., Brent R. et al. infra; Sambrook J., Fritsch E. F., and Maniatis T., supra). For cells that are grown in tissue culture (e.g., mammalian, plant, and insect cells), numerous methods for nucleic acid transfer are also available. Some methods give rise primarily to transient expression in host cells; i.e., the expression is gradually lost from the cell population. Other methods can also generate cells that stably express the transferred nucleic acid, though the percentage of stable expressers is typically lower than transient expressers. Such methods include viral and non-viral mechanisms for nucleic acid transfer.

In the case of viral transfer, a viral vector is used to carry nucleic acid inserts into the host cell. Depending on the specific virus type, the introduced nucleic acid may remain as an extrachromosomal element (e.g., adenoviruses, Amalfitano A., Begy C. R., and Chamberlain J. S.; *Proc. Nati. Acad. Sci. USA* 1996 93:3352–3356) or may be incorporated into a host chromosome (e.g., retroviruses, Iida A., Chen S. T., et al. *J Virol* 1996 70:6054–6059).

In the case of non-viral nucleic acid transfer, many methods are available (Ausubel F., Brent R. et al. 1996). One technique for nucleic acid transfer is $CaPO_4$ coprecipitation of nucleic acid. This method relies on the ability of nucleic acid to coprecipitate with calcium and phosphate ions into a relatively insoluble $CaPO_4$ grit, which settles onto the surface of adherent cells on the culture dish bottom. The precipitate is, for reasons that are not clearly understood, absorbed by some cells and the coprecipitated DNA is liberated inside the cell and expressed. A second class of methods employs lipophilic cations that are able to bind DNA by charge interactions while forming lipid micelles. These micelles can fuse with cell membranes, delivering their DNA cargo into the host cell where it is expressed. A third method of nucleic acid transfer is electroporation, a technique that involves discharge of voltage from the plates of a capacitor through a solution containing DNA and host cells. This process disturbs the bilayer sufficiently that DNA contained in the bathing solution is able to penetrate the cell membrane.

Several of these methods often involve the transfer of multiple DNA fragments into individual cells. It is often difficult to limit the quantity of DNA taken up by a single cell to one fragment. However, by using "carrier" nucleic acid (e.g., DNA such as herring sperm DNA that contains no sequences relevant to the experiment), or reducing the total amount of DNA applied to the host cells, the problem of multiple fragment entry can be reduced. In addition, the invention does not specifically require that each recipient cell have a single type of library sequence. Multiple passages of the library through the host cells (see below), permit sequences of interest to be separated ultimately from sequences that may be present initially as bystanders. Moreover, the presence of multiple independent vector/insert constructs in a cell may be an advantage in certain cases because it allows more library inserts to be screened in a single experiment.

For microbial cells such as bacteria and fungi, general methods such as electroporation work very well. In addition, methods have been customized to specific organisms— many of which involve pretreatment of the cells with salts (e.g., LiOAC for *S. cerevisiae*, $CaCl_2$ or $RbCl_2$ for *E. coli*). These methods are known in the art (Ausubel et al., 1996; Sambrook et al., 1989).

F. Screen By Flow Sorter

An important benefit of the present invention involves the ability to quantify the characteristics of a library that is generated in an autofluorescent protein scaffold. To do this, a flow sorter or similar device may be used, as such devices are capable of rapidly examining a large number of individual cells that contain library inserts (e.g., 10–100 million cells per hour) (Shapiro H. *Practical Flow Cytometry* 1995).

Fluorescence measurements of the library expressed in particular host cells preferably involve comparisons with controls; for example, host cells that lack the expression construct (negative controls), and host cells that express the autofluorescent protein using the same expression vector in which the library is constructed, but without any inserted sequence in the autofluorescent protein (positive controls). These controls set limits on both the low (background) fluorescence end of the spectrum, and the high end. From these initial measurements, mean levels of fluorescence can be determined, as well as a rough gauge of the variance of the distribution. For instance, the wild type autofluorescent protein may be expressed such that a mean fluorescence intensity of 1000x is attained in the specific expression vector and host cells used in the experiment; the host cells without the expression vector may have a mean (background) fluorescence intensity of x. The scaffold that contains a linker appropriate for insertion may have a mean intensity that is 100x, and the scaffold plus library may have a mean intensity that is 25x. In addition, the standard deviation of the library fluorescence intensity distribution may be roughly +/−20x.

It may be desirable also to compare mean fluorescence levels with biochemically determined levels of autofluorescent protein with and without inserted foreign sequence(s). For example, a western blot comprising lanes with various dilutions of purified (or at least known amounts of) autofluorescent protein (e.g., GFP) may be run beside a lane prepared from a cell lysate of host cells that harbor the expressed library to provide a biochemical estimate of autofluorescent expression levels in host cells. A monoclonal antibody directed against an epitope that is preserved in the scaffold protein can be used to bind the protein present on the blot and can be indirectly visualized by an appropriately labeled second antibody according to methods known in the art (Ausubel et al., 1996; Sambrook et al., 1989). This allows correlation of mean fluorescence intensity values with the mass of the scaffold protein in cells. From such experiments, the approximate cytoplasmic concentration of library sequences expressed in cells may be calculated. This in turn may permit estimation of the dissociation/inhibition constants that are most likely to apply to perturbagen/target interactions within the cell (see below).

The procedures for quantitation and screening described above can be applied both to the preparation of scaffold candidates, and to the generation of insertional libraries using the scaffold candidates as insertion or fusion partners. Thus, scaffold proteins that contain linkers inserted at defined or random positions can be tested for fluorescence properties. The scaffolds that exhibit good quantitative behavior (e.g. consistent, robust expression in a variety of different host cells) according to the flow cytometry readouts can be further examined after a library of sequences has been inserted into the linker site.

These quantitative measurements provide useful information about the expression library. The measurements permit estimates of library diversity (defined here as the fraction of individual inserts that express significant levels of scaffold protein multiplied by the total number of independent clones in the library), qualitative assessment of the robustness of particular scaffold proteins, and evaluation of the relative and absolute levels of scaffold expression in a bulk population of cells and in individual cells.

G. Selection By Flow Sorter

The flow sorter has the ability not only to measure fluorescence signals in cells at a rapid rate, but also to collect cells that have specified fluorescence properties. This feature may be employed in a preferred embodiment of the invention to enrich the initial library population for sequences that have predetermined characteristics. For example, a library created by insertion of a set of oligonucleotides of random sequence into the autofluorescent protein coding sequence will include a percentage of sequences that contain termination codons. This percentage can be minimized by biasing the library inserts against having an A in the third position of a codon to reduce the incidence of termination codons in the inserts. In all likelihood, however, some sequences with termination codons will be present in the library. Expression of such sequences within cells will result in truncated scaffold proteins that likely are no longer fluorescent. In addition, there may be other library sequences that for different reasons do not produce fluorescent proteins inside cells; for instance, the scaffold protein plus insert may fold incorrectly or may be digested rapidly by proteases within the cell. These library sequences that result in non-fluorescent protein may be easily eliminated from the library set by collecting cells on the cell sorter which express levels of fluorescence above a predetermined threshold criterion. Such a selection procedure improves the quality of the library by removing those members that are most likely not to produce functional proteins. Typically libraries of more than a few million clones are difficult to construct and screen in vivo. Thus, in some cases a premium may be placed on ensuring that the maximum number of library sequences express stable proteins. The selection experiments can be performed in a variety of host cells such as yeast, bacteria, plant, insect, or mammalian cells depending on the requirements of the experiment and the capabilities of the expression vectors being used.

In certain cases it may be desirable to enrich the library for sequences that are compatible with very high levels of expression of the scaffold protein. It is possible, even likely, that expression of a diverse set of sequences carried in a scaffold protein will generate a wide range of expression levels in cells due to different stabilities, folding tendencies, etc. This can be visualized on the flow sorter as a broadening of the distribution of fluorescence intensities. The distribution may range from background to the mean expression of the wild type autofluorescent protein expressed under the same conditions as the library, and beyond. To bias the library toward sequences compatible with the highest levels of protein expression, cells may be collected on the flow sorter that fall near the extreme right ("bright") end of the fluorescence intensity distribution. This process can be repeated in order to further skew the library population toward those that are expressed at the highest levels in the host cells. Such a procedure may be useful, if for example, the genetic experiments described below rely on expression of perturbagen molecules in cells at very high levels. The enrichment of the library may be achieved by examination of library-containing cells of different types (e.g., yeast, bacteria, plant, insect, or mammalian) depending on the objective of a particular experiment.

H. Peptide/Protein Fragment Display as Perturbagens

Perturbagens as defined supra behave in a transdominant mode to interfere with native functions of cellular components in vivo. For the purposes of the present invention, perturbagens take the form of proteins, protein fragments, and peptides (as disclosed in co-owned Ser. No. 08/812,994, Methods for Identifying Nucleic Acid Sequences Encoding Agents that Affect Cellular Phenotypes, filed Mar. 4, 1997). Perturbagens have the advantage that, when overexpressed, they can produce a mutant phenocopy by inhibiting the products of both allelic gene copies in cells. In this manner, they overcome one limitation of conventional genetic analysis in diploid cells; namely, the difficulty of isolating recessive mutants. Furthermore, DNA sequences that encode perturbagens are easily recovered from cells by, e.g., PCR. In addition, the target of the perturbagen in vivo can be readily identified using the perturbagen itself as a probe. Biochemical methods of purification or, preferably, yeast two-hybrid analysis provide convenient tools to elucidate perturbagen/target interactions. Unlike mutations induced within genes that reside on chromosomes, it is relatively straightforward to identify the target of the perturbation, and hence, the mechanism that underlies the phenocopy trait.

As described above, insertional fusions that involve autofluorescent proteins have numerous advantages as display scaffolds for peptides or protein fragments. These proteins permit careful, rigorous measurement of the quantitative characteristics of perturbagen libraries prepared with them. Manipulation of the perturbagen library to enrich for sequences compatible with high expression levels and cell-by-cell monitoring of perturbagen expression are readily achieved. One of the most significant uses of the method disclosed herein involves the use of autofluorescent proteins as scaffolds that can present perturbagens in vivo. These perturbagen libraries provide, in essence, the means for genetic analysis that can be applied in virtually all cells—as long as they can be cultured and exogenous nucleic acid can be expressed within them.

EXAMPLE 1

Construction of Peptide Display Libraries in the Interior of GFP

An attractive strategy for the presentation of aptamers in cells involves the insertion of aptamers into a protein scaffold such that upon expression the aptamers are exposed on the surface of the scaffold. Immunoglobulins (Igs) provide a useful analogy for this type of approach. The tertiary structure of the variable domain of an Ig subunit is composed of a beta-barrel together with three exposed loops which form hypervariable regions. These loops comprise antigen binding sites and can accommodate a vast number of different sequences. Presumably, the rigidity and stability of the beta-barrel structure facilitates the presentation of exposed loops such that the variable peptide sequences assume unique, stable conformations. The recently-solved crystal structure of GFP reveals that this protein also assumes a beta-barrel structure and has a number of solvent-exposed loops (Ormo et al., 1996). These loops are candidate sites for the insertion of random aptamers. By inserting aptamers into a number of the loops in GFP, it is possible to identify "ideal" loops which can accommodate and present random aptamers while allowing GFP to retain its autofluorescent properties.

Preparation and Testing of GFP Yeast Scaffold Candidates
pVT21, which permits induction of GFP expression in the presence of galactose, was obtained by manipulation of pACA151, a 6.7Kb 2 μ yeast shuttle vector which contains markers for URA3 and ampicillin resistance. In addition it contains a GFP expression cassette made up of the GAL 1.10 promoter, the coding region of a red-shifted (S65T) GFP gene, and the phosphoglycerate kinase (PGK1) 3' end. To construct pVT21, the EcoRI site in pACA 151 was converted into a BglII site. In addition, the PGK1 3' end fragment of pACA 151 was replaced with a 700 bp fragment (containing NarI and BglII ends) which contained the PGK1 3' end with termination codons in three reading frames.

Using the crystal structure of GFP as a guide, ten positions on the protein which fall within exposed loops were chosen as potential aptamer insertion sites. FIG. 1. Into the corresponding regions of the GFP gene, recognition sequences for BamHI, EcoRI and XhoI restriction endonucleases were introduced yielding plasmids pVT22–pVT31. Table 1. pVT21 was used as the parent vector for pVT22–pVT31. In order to construct pVT22, pVT21 was used as a template in two separate PCR reactions using primer pairs OVT329, OVT307, and OVT330 and OVT317. The termini of the resulting fragments contained XhoI-EcoRI and BamHI-EcoRI restriction sites, respectively. These two fragments were digested with EcoRI (NEB), ligated using T4 DNA ligase (Boehringer Manheim), and PCR amplified using primers OVT329 and OVT330. The resulting 2 Kb fragment contained the GAL1 UAS and PGK1 3' UTR, as well as a GFP gene with a 6-codon insert corresponding to XhoI-EcoRI-BamHI recognition sequences. pVT22 was obtained by digesting this 2 Kb fragment with PstI and HindIII and inserting it into the pVT21 backbone (also digested with PstI and HindIII). pVT23–pVT31 were constructed using an identical cloning strategy except that, instead of OVT307 and OVT317 the following primers were used: pVT23 (OVT308, OVT318), pVT24 (OVT309, OVT319), pVT25 (OVT310, OVT320), pVT26 (OVT311, OVT321), pVT27 (OVT312, OVT322), pVT28 (OVT313, OVT323), pVT29 (OVT314, OVT324), pVT30 (OVT315, OVT325), pVT31 (OVT316, OVT326). Table 2.

TABLE 1

Sites of insertion within the GFP gene of pVT22-pVT31 of an 18 nucleotide fragment coding for the hexapeptide Leu-Glu-Glu-Phe-Gly-Ser. Amino acids numbering is according to the wild type GFP gene.

| Construct | Insertion Site |
|---|---|
| pVT22 | Thr49-Thr50 |
| pVT23 | Met78-Lys79 |
| pVT24 | Gly116-Asp117 |
| pVT25 | Lys140-Leu141 |
| pVT26 | Gly134-Asn135 |
| pVT27 | Gln157-Lys158 |
| pVT28 | Glu172-Asp173 |
| pVT29 | Leu194-Leu195 |
| pVT30 | Gly189-Asp190 |
| pVT31 | Glu213-Lys214 |

Figure 2:
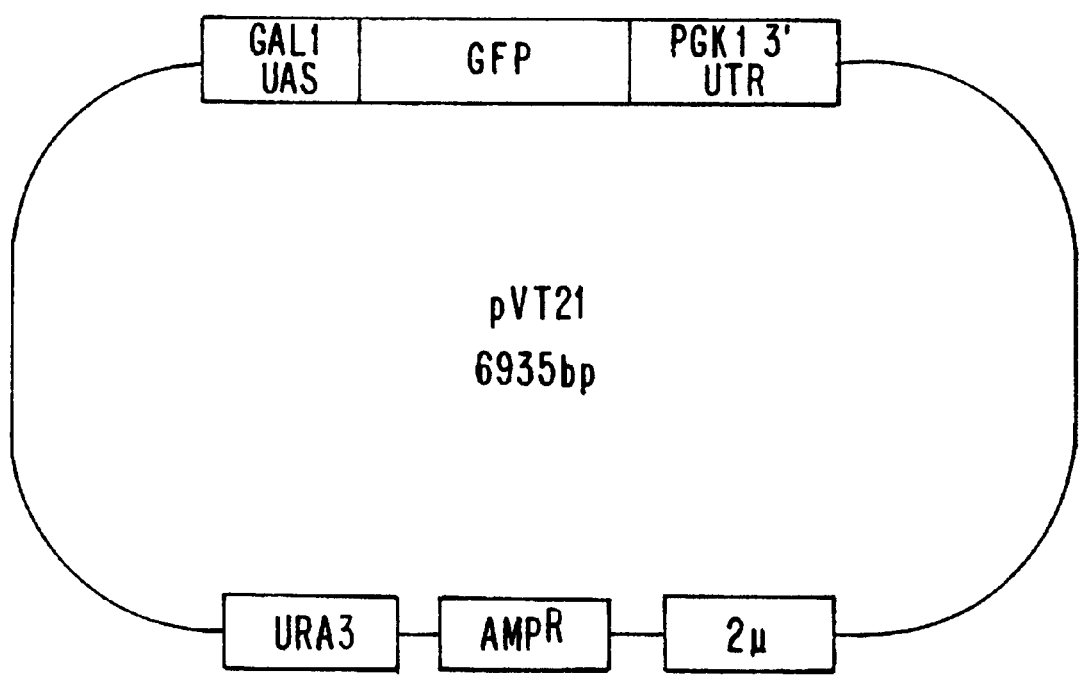
FIG. 2: Map of pVT21.

This yielded ten GFP constructs, each of which contained six additional codons that included the restriction sites. These constructs were grown in E. coli and introduced into the yeast expression vector pVT21. FIG. 2. Yeast transformations were performed using the lithium acetate method (Gietz, R. and Schiestl, R. 1995 Methods in Molecular and Cellular Biology 5:255–269), and transformations were selected and maintained on standard synthetic medium lacking uracil.

Figure 3:
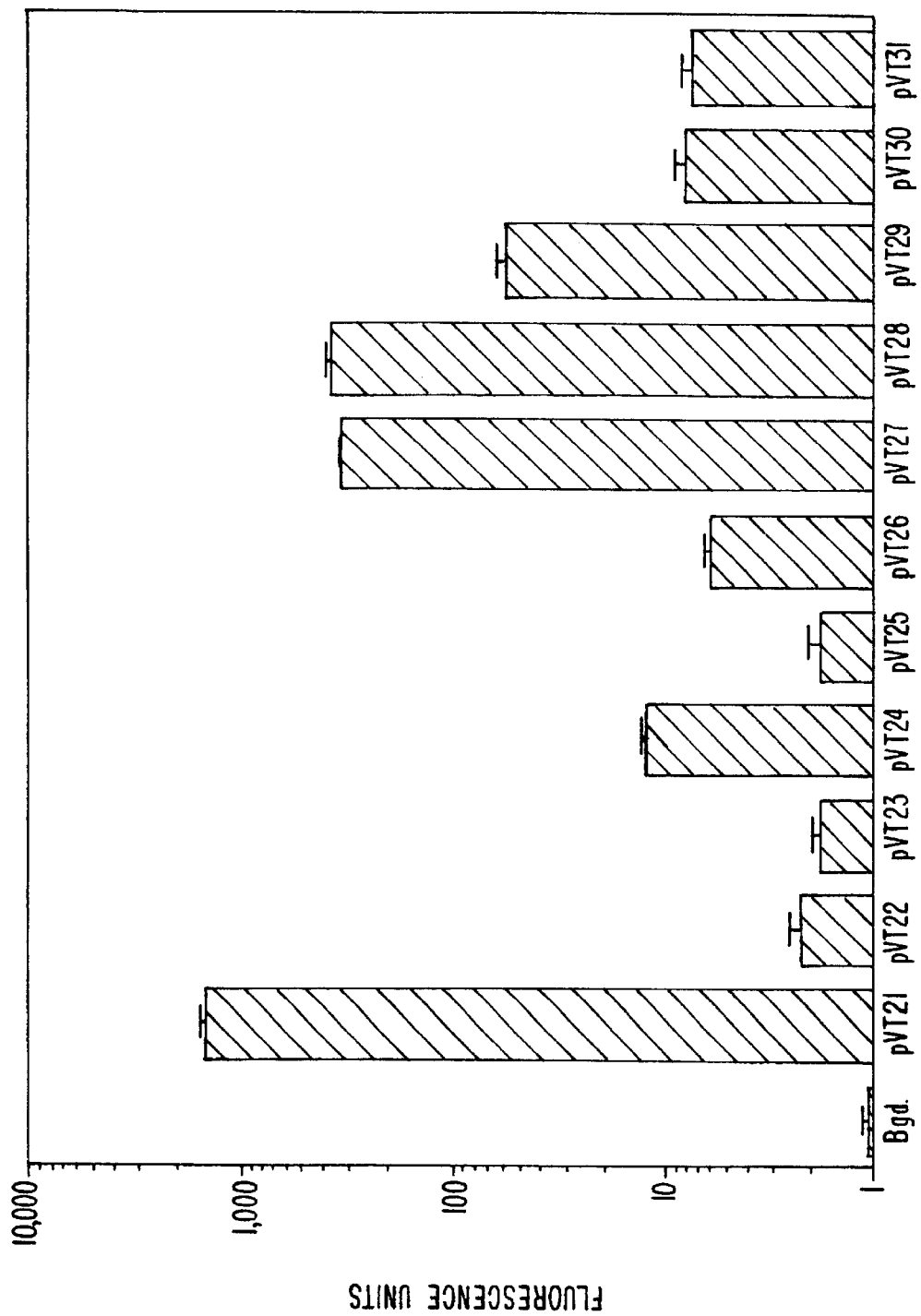
FIG. 3: Mean fluorescence intensities of cell populations harboring GFP scaffold candidates, and various controls.

The resulting transformed yeast were grown under inducing conditions (i.e., galactose-containing media) to drive expression of the GFP hybrid proteins and analyzed by flow sorter to gauge the levels of GFP fluorescence. FIG. 3 and Table 3. Of the ten scaffold candidate constructs examined, the GFP constructs which retained maximal fluorescence (pVT27, pVT28, and pVT29) were chosen as candidates to insert aptamers within the XhoI and BamHI restriction sites.

TABLE 2

Oligonucleotides. Restriction sites are underlined.

| Primer | Nucleotide Sequence |
|---|---|
| OVT309: | TGA<u>GAATTCCTCGAG</u>ACCTTCAAACTTGACTTCAGC |
| OVT310: | TGA<u>GAATTCCTCGAG</u>TCCATCTTCTTTAAAATCAATAC |
| OVT311: | TGA<u>GAATTCCTCGAG</u>TTTGTGTCCAAGAATGTTTCCATC |
| OVT312: | TGA<u>GAATTCCTCGAG</u>TTGTTTGTCTGCCATGATGTATAC |
| OVT313: | TGA<u>GAATTCCTCGAG</u>TTCAATGTTGTGTCTAATTTGAAG |
| OVT314: | TGA<u>GAATTCCTCGAG</u>GCCAATTGGAGTATTTTGTTGAT |
| OVT315: | TGA<u>GAATTCCTCGAG</u>AAGGACAGGGCCATCGCC |
| OVT316: | TGA<u>GAATTCCTCGAG</u>TTCGTTGGGATCTTTCGAAAG |
| OVT317: | TGA<u>GAATTCGGATCC</u>ACTGGAAAACTACCTGTTCCATGG |
| OVT318: | TGA<u>GAATTCGGATCC</u>AAACGGCATGACTTTTCAAGAG |
| OVT319: | TGA<u>GAATTCGGATCC</u>GATACCCTTGTTAATAGAATCG |
| OVT320: | TGA<u>GAATTCGGATCC</u>AACATTCTTGGACACAAATTGG |
| OVT321: | TGA<u>GAATTCGGATCC</u>TTGGAATACAACTATAACTCACAC |
| OVT322: | TGA<u>GAATTCGGATCC</u>AAGAATGGAATCAAAGTTAACTTC |
| OVT323: | TGA<u>GAATTCGGATCC</u>GATGGAAGCGTTCAACTAGC |
| OVT324: | TGA<u>GAATTCGGATCC</u>GATGGCCCTGTCCTTTTACC |
| OVT325: | TGA<u>GAATTCGGATCC</u>TTACCAGACAACCATTACCTG |
| OVT326: | TGA<u>GAATTCGGATCC</u>AAGAGAGACCACATGGTCC |
| OVT329: | GTTAGCTCACTCATTAGGCACCC |
| OVT330: | CGGTATAGATCTGTATAGTTCATCCATGCCATGTG |
| APT1: | GGCCT<u>AGGATCC</u> |
| APT2: | TGA<u>CTCGAG</u>(NN(G/C/T))$_{20}$<u>GGATCCT</u>AGGCC |

TABLE 3

Mean fluorescence intensities of cell populations harboring pVT27APT, pVT28APT, pVT29APT and parent constructs. Fluorescence gates were set either at background (Bgd.), or at a value ten-fold higher than background (10X Bgd.) Background is defined as the minimum fluorescence intensity value which is larger than the fluorescence value of 99% of non-induced cells.

| GFP CONSTRUCT | Fluorescence > 1X Bgd.[1] | | Fluorescence > 10X Bgd. | |
|---|---|---|---|---|
| | % Total Population | Mean (FU$_2$) | % Total Population | Mean (FU) |
| pVT21 (Dex.) | 1 | 3 | 0 | — |
| pVT21 | 96 | 1545 | 95 | 1565 |
| pVT27 | 89 | 378 | 81 | 414 |
| pVT27 APT | 39 | 41 | 15 | 99 |
| pVT28 | 86 | 428 | 78 | 471 |
| pVT28 APT | 42 | 28 | 13 | 78 |
| pVT29 | 77 | 71 | 59 | 90 |
| pVT29 APT | 32 | 7 | 2 | 37 |

Preparation of Peptide Display Libraries

DNA oligonucleotides coding for random 20 amino acid aptamers were synthesized and inserted into the XhoI and BamHI sites of the three selected GFP constructs mentioned above. 1 pmole of APT1 (Table 2) was annealed to 1 pmole APT2 (Table 2) and the second strand was synthesized using Klenow fragment (Promega, Madison Wis.). The resulting double stranded aptamers consisted of BamHI and XhoI sites flanking 60 bases of biased random sequence. The GFP-aptamer libraries in each of the three scaffold candidates were created by digesting the aptamers with BamHI and XhoI, inserting them into BamHI/XhoI cut vector (either pVT27, pVT28, or pVT29) and transforming the construct into *E. coli*. A total of about 2,000 individual clones were selected from each library for testing purposes. For each set of scaffold candidates, 20 random clones were examined to determine the percentage of insert-bearing clones. All three had insert frequencies of at least 90%.

Evaluation of Peptide Display Libraries In Yeast

The amplified libraries from *E. coli* were transferred into yVT12 yeast cells (MATa, HMLa, HMRa, sst2Δ, mfa1Δ::hisG, mfa2Δ::hisG, ade2-1, leu2-3, lys2, ura3-1, STE3::GAL1-STE3::HIS3), derived from JRY5312 (Boyartchuk, V., Ashby, M. et al., 1997 275:1796–1800). yVT12 cells containing the appropriate plasmid (or library) were plated onto selective media supplemented with 2% dextrose or 2% galactose/2% raffinose. Following incubation at 30° C., yeast derived from a single colony (or, in the case of a library, from a patch of cells) were transferred into selective liquid media supplemented with the appropriate carbon source. These cultures were grown with shaking at 30° C. until mid log phase. The yeast were pelleted, resuspended in PBS, and scanned on a FACStarPLUS (Becton & Dickinson, San Jose Calif.) scanner with excitation at 488 nm. Fluorescence emission was measured with a 515/40 nm band pass filter. Cytometer settings were: FSC E00V, SSC 400V, FL1 470V, FSC threshold value 24. All scans were repeated in independently cultured cells in triplicate. Though the absolute fluorescence levels of different cells varied, the fluorescence appeared to be uniformly distributed throughout the cells, not concentrated in clumps or subcellular compartments. This suggested that the GFP-aptamer hybrid proteins were soluble in yeast.

To determine which of the three sites within GFP can best accommodate peptides comprising 20 residues of diverse sequence, fluorescence scans on a flow cytometer were carried out. Mean fluorescence intensities and the fraction of cells in specific fluorescence intensity windows were determined for yeast cell populations containing the libraries (see Table 3). The results suggested that two candidates (pVT27APT and pVT28APT) provided a suitable site for library expression using GFP as a scaffold, according to the method of scaffold design pursued in these experiments. The other scaffold-aptamer library (PVT29APT) had a fluorescence intensity that was close to the background level. Thus, of the sites we examined in GFP (apart from the N- and C-termini), two were found to display a variety of peptide aptamers in a manner compatible with autofluorescence. One of these sites (corresponding to pVT27) is located within one of the smaller loops of the protein (Ala155-Ile161). However, main chain atoms in this loop have the highest temperature factors of any backbone atoms in the structure, as high as the solvent-exposed N-terminus. This suggests that the insertion site is more mobile than other loops and, as such, may not be an integral part of the structure.

Figure 4:
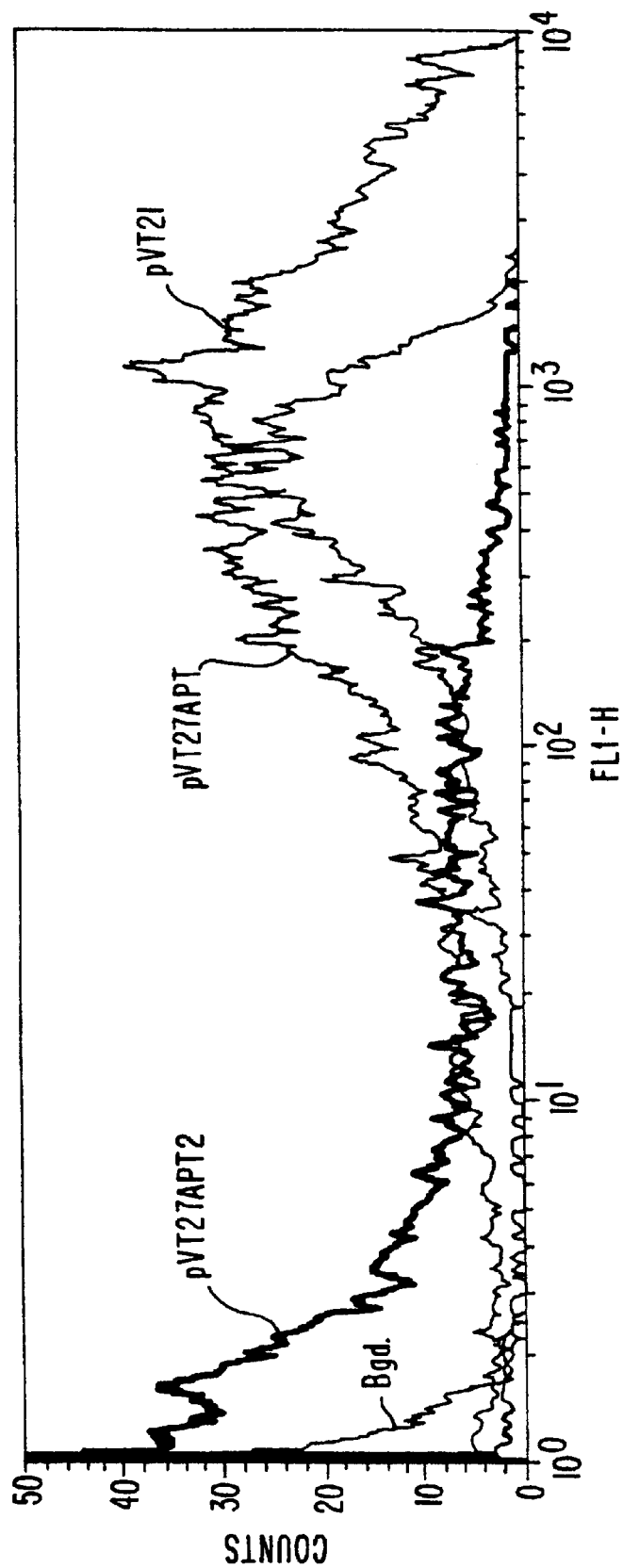
FIG. 4: Fluorescence intensity scan of pVT21, pVT27, and pVT27APT2. Bgd: pVT21—containing yeast, grown under repressing conditions (dextrose).

The library species in pVT27APT and pVT28APT each had a mean fluorescence intensity that was roughly 10% of the construct containing the linker sequence alone. A fluorescence window was set to determine whether pVT27APT and pVT28APT clones generally produced low fluorescence intensities, or whether there was a wide range of intensities. At an intensity cutoff ten-fold above the background (cells without GFP) where 95% of the control GFP-expressing yeast (with pVT21) were above threshold, nearly 15% of the pVT27APT-and pVT28APT-containing cells were also positive. This suggests that; (i) pVT27APT and pVT28APT clones encode proteins that are either expressed at lower levels than wild type GFP produced by pVT21, or are less fluorescent; and (ii) there is significant variability in fluorescence among the individual library clones.

pVT27 was chosen as a scaffold candidate to build a large GFP-aptamer library. To facilitate this, an oligonucleotide coding for a biased random 15 amino acid aptamer (flanked by three constant amino acids on either end) was synthesized and cloned into pVT27 (as described above under preparation of Peptide Display Libraries). The resulting library contained 1.5×10$^6$ members and was designated pVT27APT2. A proportion of yeast harboring pVT27APT2 GFP-aptamer clones did not fluoresce when grown under inducing conditions. FIG. 4. These dim yeast may have lacked fluorescence due to termination codons in the random aptamer, improper folding of the full-length GFP-aptamer protein, or for other reasons. Based on the biased random DNA sequence encoding the aptamer, 27% of the library members were expected to contain termination codons by chance, resulting in a truncated and non-fluorescent GFP protein. From the fluorescence intensity profiles, it was estimated that roughly 60% of the library sequences produced non-fluorescent proteins. The difference (60%–27%) may reflect the proportion of incorrectly folded and/or unstable GFP proteins in the library. These approximate numbers were corroborated by DNA sequence analysis of 15 individual GFP-aptamer clones.

Figure 5A:
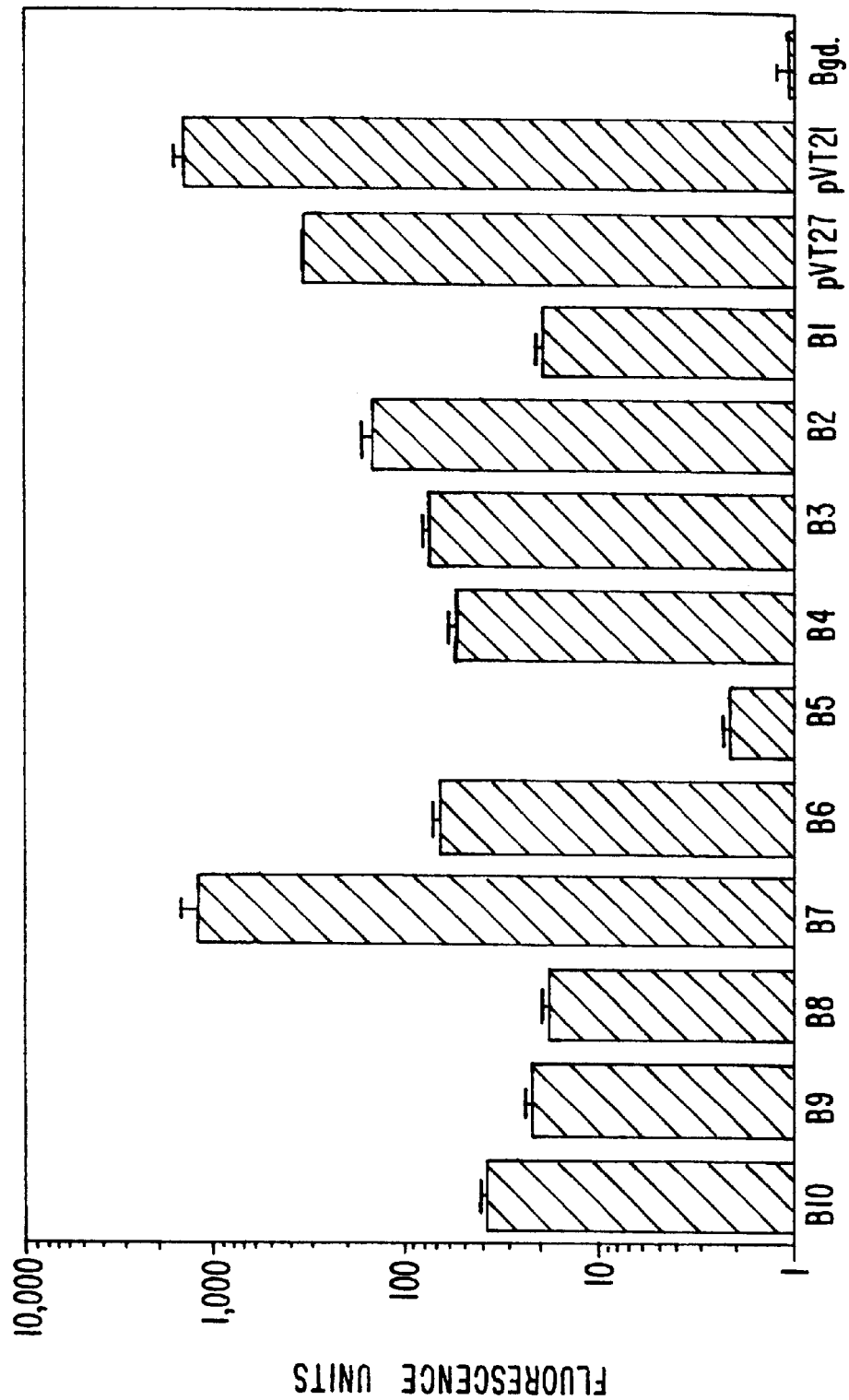
FIG. 5A: Mean fluorescence intensities of 10 sorted pVT27APT2 yeast clones (B1–B10).

To further explore the question of the folded state of GFP-aptamer molecules produced by the pVT27APT2 library, the fluorescence properties of 10 individual clones were examined in detail. These yeast were obtained by collecting a subpopulation of the pVT27APT2 yeast library which was fluorescent at a level above that of induced cells. The sorted yeast clones were grown under inducing conditions, and fluorescence emission at 515 nm was measured. Wild type GFP protein has excitation and emission maxima at 395 nm and 509 nm, respectively. pVT21 and its derivatives produce a red-shifted GFP variant which has an excitation maximum at 490 nm but also emits at 509 nm. Fluorescence analysis of the 10 clones with excitation at 488 nm revealed a broad distribution of mean fluorescent values. FIG. 5A.

Figure 5B:
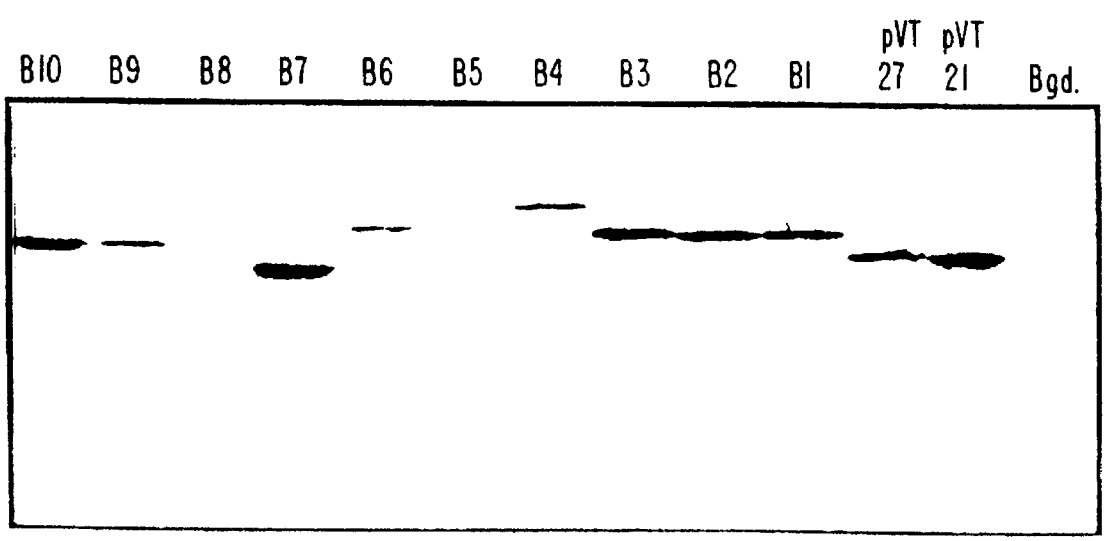
FIG. 5B: Western blot analysis of GFP-aptamers from 10 pVT27APT2 yeast clones.

A Western blot of proteins extracted from yeast cells harboring these 10 clones was prepared to provide an independent estimate of GFP-aptamer levels in these cells. SDS-PAGE was carried out with the Laemmli Tris-buffer system. (Laemmli, U. *Nature* 1970 277:680–685) Gel transfer was performed using a Genie electrophoretic blotter (Idea Scientific). Following blotting, the membrane was incubated successively with rabbit antisera containing polyclonal anti-GFP antibodies (Clontech, Palo Alto Calif.), and peroxidase conjugated anti-rabbit IgG (Santa Cruz Biotechnology, Santa Cruz Calif.); and the bands were visualized with the peroxidase substrates diamino benzadine and hydrogen peroxide. There was a rough correlation between expression and fluorescence levels. For example, clone B5 produced the least fluorescence of any of the 10 clones examined, more than 100 fold below the parental pVT27 construct. The protein level revealed by Western blot analysis was also the lowest of the 10 clones. FIG. 5B.

The possibility of serious bias in the sequences of aptamers capable of display by the pVT27 GFP scaffold was examined by sequence analysis of 53 independent clones from the pVT27APT2 library. Table 4. These clones were selected from the subset of pVT27APT2 sequences that generate fluorescent proteins by selection using the flow sorter. Analysis of the amino acid distribution of these aptamers revealed some statistically significant bias. Glycine, lysine, and threonine were over-represented, compared to their expected frequency of occurrence, while leucine and glutamate were under-represented. Glycine was one of the most dramatic outliers, and this may reflect a preference for small, flexible residues in protein loops. (Edwards, M., Stenberg, J. et al. *Protein Eng:* 1987 1:173–181) Indeed, overabundance of glycine at position 12 in the aptamer was the only statistically significant difference (p<0.005) observed when the analysis was performed position by position in the 15-residue aptamer sequence. However, it seems unlikely that there is a dramatic bias in the structural/chemical properties encompassed by the aptamer library in terms of charge or hydrophobicity, because no systematic preference for or avoidance of residues of specific chemical types was observed.

Analysis of amino acid composition of aptamer sequences among 53 randomly selected clones encoding "bright" GFP chimeras.

| AMINO ACID | EXPECTED # | OBSERVED # | OBS/EXP | p |
|---|---|---|---|---|
| Ala | 48.7 | 46 | 0.95 | 0.68 |
| Arg | 64.9 | 66 | 1.09 | 0.18 |
| Asn | 32.5 | 34 | 1.05 | 0.75 |
| Asp | 32.5 | 36 | 1.11 | 0.68 |
| Cys | 32.5 | 28 | 1.11 | 0.68 |
| Gln | 16.2 | 15 | 0.93 | 0.87 |
| Glu | 16.2 | 28 | 0.86 | 0.041 |
| Gly | 48.7 | 92 | 1.89 | <0.001 |
| His | 32.5 | 24 | 0.74 | 0.38 |
| Ile | 32.5 | 40 | 1.23 | 0.43 |
| Leu | 64.9 | 8 | 0.12 | <0.001 |
| Lys | 16.2 | 33 | 2.03 | 0.002 |
| Met | 16.2 | 27 | 1.67 | 0.071 |
| Phe | 32.5 | 25 | 0.77 | 0.46 |
| Pro | 48.7 | 43 | 0.88 | 0.59 |
| Set | 81.3 | 66 | 0.81 | 0.18 |
| Thr | 48.7 | 69 | 1.42 | 0.018 |
| Trp | 16.2 | 27 | 1.67 | 0.071 |
| Tyr | 32.5 | 20 | 0.62 | 0.097 |
| Val | 48.7 | 52 | 1.07 | 0.65 |

Preparation and Evaluation of Peptide Display Libraries in Mammalian Cells

The above libraries and screening methods may be readily adapted for evaluation of mammalian cells, using materials and techniques that are familiar to those of skill in the art.

Although a wide variety of genes encoding GFP are suitable for use in the methods described herein, a GFP—encoding gene that was human codon—optimized (E-GFP, available from, e.g., Clontech Catalog 98/99 No. 6077-1, p. 154) was selected for use in experiments in which the peptide display libraries were expressed in representative mammalian cell lines.

A suitable retroviral vector was constructed as follows. Retroviral vector pCLMFG (received from the laboratory of Dr. Inder Verma at the Salk Institute) was digested with HindIII, linearized with T4 DNA polymerase, and subsequently digested with ScaI. A 2874 bp fragment containing the retroviral elements was isolated and cloned into a 1.8 kb PvuII, SspI digested Bluescript fragment that contains the bacterial origin of replication and an ampicillin resistance gene (commercially available through Stratagene, Inc.). This vector was designated pVT323. The Clontech vector containing E-GFP and pVT323 each were digested with NcoI and BamHI and religated. Plasmids containing the E-GFP and pVT323 inserts in the correct orientation were isolated and designated as vector pVT324. Restriction sites just 3' of the E-GFP fragment were altered by cloning double stranded oligonucleotides (sense sequence 5' CGAGAATATTG-GAAGCTTGGGCGGCCGCGGATCCAGTGAATGAGT GC-3') into the XhoI and BamHI sites. This insertion also added stop codons in all three frames. This plasmid vector was designated pVT325.

Following the strategy described above for the construction of yeast scaffold vector pVT27, a modified E-GFP gene containing an internal 6-codon insert encoding the XhoI, HindIII and BamHI sites was placed under the control of a CMV promoter by cloning the gene into the NcoI and BglII restriction sites of plasmid vector pVT325. This plasmid vector was designated pVT334. Next, a library of DNA fragments encoding random 15 amino acid sequences were inserted into the XhoI and BamHI sites of the E-GFP gene of pVT325, using an identical cloning strategy as was described above for the construction of the random peptide library in pVT27APT2. The resulting library contained $7 \times 10^7$ members.

Figure 7:
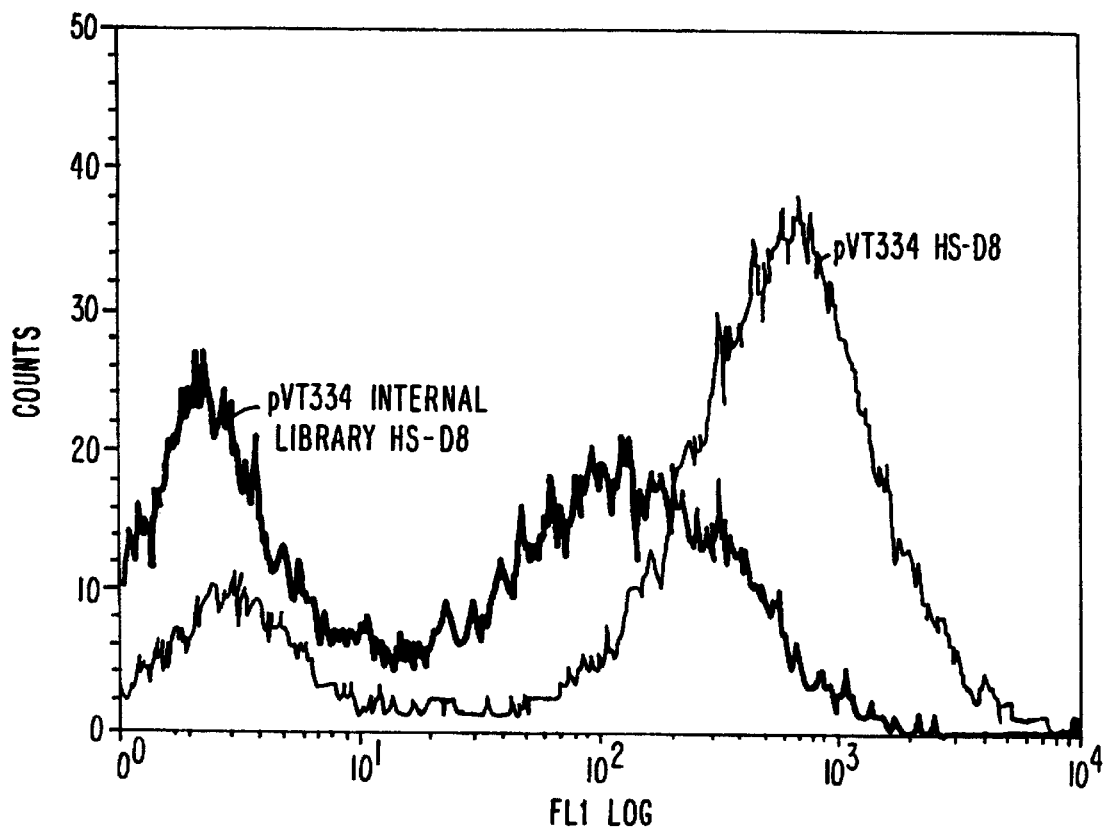
FIG. 7: Fluorescence intensity scan of HS294T p16 lacI cells expressing either E-GFP alone (pVT334), or E-GFP bearing internal insertions of DNA encoding 15 amino acid random peptides.

The fluorescence properties of the pVT334 library bearing DNA inserts encoding the random 15 amino acid library was evaluated by analyzing a random sampling of cells from that library. Three separate human melanoma cell lines (HS294T p16 lacI, WM35 and 1552C) were infected with viral supernatant from the pVT334 library. A representative fluorescence scan from the eighth day post-infection is provided in FIG. 7. This scan demonstrates that the infection and subsequent expression of the 15 amino acid library variants can be monitored in human cells by this technique. Moreover, the data suggests that the GFP/library variant constructs are stable over time. As with the pVT27APT2 library, a dim population was present, and may either represent uninfected cells, or incorrectly folded, unstable or prematurely terminated constructs.

Figure 8:
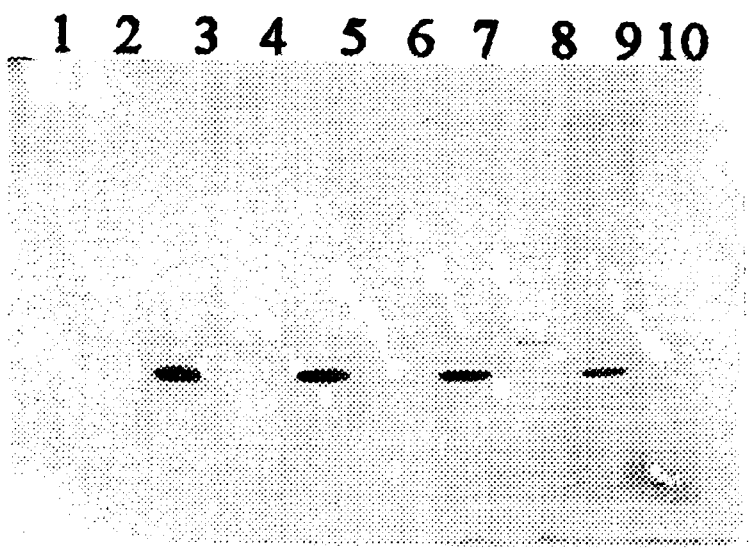
FIG. 8: Western blot analysis of HS294T p16 lacI clones expressing E-GFP variants, as follows: marker (lane 1); 25 µl control of non-infected cells (lane 2); 5 µl of day-two pVT334 (lane 3); 25 µl of day-two internal library (lane 4); 5 µl of day-eight pVT334 (lane 5); 25 µl of day-eight internal library (lane 6); 5 µl of day-eight pVT334 (lane 7); 25 µl of day-eight internal library (lane 8); 3 µl of day-two pVT334 (lane 9); 25 µl of day-two internal library (lane 10).

A Western blot of proteins extracted from melanoma cells transformed with the pVT334-internal library construct was prepared using an aliquot of the cells used in FACS analysis described above (FIG. 7). Cells were harvested two and eight days post infection by trypsinization, washed in phosphate buffered saline, and resuspended in 1×gel loading buffer at a concentration of 10 cells/ml. Protein extracts were electrophoresed in a 10% Bis-Tris NuPage gel (Novex, San Diego, Calif.) and transferred to PVDG membrane (Millipore Corp., Bedford, Mass.). The membrane was probed with polyclonal anti-GFP antibodies (Clontech, Palo Alto, Calif.) followed by HRP-conjugated anti-Rabbit IgG (Santa Cruz Biotechnology, Santa Cruz, Calif.). Bands were visualized using ECL detection system (Amersham). FIG. 8. This data provides an independent estimate of GFP-aptamer levels. As can be observed in FIG. 8, shifts in molecular weight similar to those observed with pVT27APT2 in yeast were detected in protein extracted from melanoma cells expressing the internal library. This data confirms that expression of random peptides was achieved.

EXAMPLE 2

Construction of Constrained Amino- and Carboxy-terminal GFP-Aptamer Fusion Libraries A variety of experiments demonstrate that the N- and C-termini of GFP can be joined to foreign sequences without seriously compromising GFP activity (Cormack B P, Valdivia R H, Falkow S, *Gene* 1996, 173:33–38; Yang T T, Cheng L, Kain S R, *Nucleic Acids Res.*, 1996, 24: 4592–4593). These properties of GFP suggest that it is possible to transform GFP into a display scaffold for perturbagen libraries that involve insertions of library sequences near the N- and C-termnini. To ensure that the library sequences are maximally constrained in conformation, and that the maximum number of library sequences can be displayed at high level, it is preferable to introduce a sequence at the N- or C-terminus that separates the library sequences from the protein termini. Two possible strategies to identify useful sequences can be employed. First, the terminal flanking sequence can be derived from DNA encoded by synthetic oligonucleotides; or, second, the terminal sequence can be derived from native proteins found within cells.

In both cases, an expression vector containing a GFP coding sequence must be prepared in such a way that a library of perturbagen-encoding sequences can be introduced. This involves a modest amount of molecular genetic engineering. The same vector, if engineered as described below, can be used as the starting material for both strategies. This vector contains a restriction site suitable for appending the terminal sequence, be it native or synthetic DNA, and a restriction site or sites appropriate for insertion of the library sequences. For example, the vector pVT21 may be engineered using methods known in the art to contain three restriction sites located either at the 5' end of the GFP coding sequence or at the 3' end of the GFP coding sequence: EcoRI, XhoI, and BamHI. (FIG. 2).

Library Construction

A DNA fragment encoding a random 15 amino acid sequence is cloned separately into the regions encoding the N- and C-terminus of GFP in pVT21. The resulting plasmids are amplified in *E. coli* and transformed into *S. cerevisiae*. Transformed yeast that retain maximal fluorescence (relative to yeast that express the GFP gene in pVT2 1) under inducing conditions are sorted from the rest of the population on a FACS machine. Those yeast with fluorescence intensities that are significantly greater than the mean fluorescence of the population (and that approach or exceed the mean fluorescence of yeast that express GFP in the pVT21 plasmid) are collected and plated for growth of single colonies.

Yeast cells harboring plasmids that confer fluorescence are purified from individual yeast colonies and their inserts sequenced. To choose suitable N- or C-terminal fusion sequences that satisfy the requirements of the invention, several criteria are considered. First, the terminal sequences must permit high-level expression and fluorescence of GFP molecules that include random peptide sequences positioned between the terminal sequence and the native GFP sequence. In addition, the ideal 15 amino acid extension sequence should preferably not be extremely charged or hydrophobic so as not to interact with cellular components.

Five (or more) plasmids are selected on the basis of their amino acid sequence composition. Random aptamers are inserted into each of these five constructs between the terminal sequence addition and the body of GFP, and the resulting libraries transformed into yeast. The transformed yeast are grown under inducing conditions and scanned using a FACS. The plasmid which best accommodates random inserts while retaining fluorescence is chosen based on its mean and median fluorescence intensities compared to controls such as the background fluorescence of yeast and the mean fluorescence of pVT21-containing yeast cells. This scaffold is used to construct a large-scale random aptamer library using methods known in the art (Ausubel et al., 1996) and as described in Example 1.

EXAMPLE 3

GFP Fusions Composed of N- or C-Terminal Fab Domains that Present Peptide Aptamers.

Higher mammals can generate antibodies capable of binding specifically and tightly to almost any compound. As such, immunoglobulins (Igs) can be considered as ideal protein scaffolds for the display of short peptide aptamers. The variable domain of an Ig subunit consists of a beta-barrel together with three exposed loops that form hypervariable regions (HVRs) (Edmundson, A., Ely, K. et. al. 1975 *Biochemistry* 14:3953–3961). These HVRs comprise the antigen binding sites and, depending on the class of Ig, can accommodate between 6 and 15 amino acids of random sequence.

Recently, Igs have been engineered to produce minibodies (Pessi, A., Bianchi, E. et. al. 1993 *Nature* 362:37–369). A minibody is a 61 amino acid polypeptide consisting of three strands from each of the two beta sheets of the Fab variable domain of the mouse immunoglobulin, together with the H1 and H2 hypervariable regions. H1 and H2 can each display a random peptide sequence of 6 amino acids. Furthermore, it has been demonstrated (using phage display) that a minibody library can be used to isolate a minibody which binds tightly and specifically to human interleukin-6 (Martin, F., Toniatti, C. et. al. 1994 *EMBO Journal* 13:5303–5309). These properties of a minibody suggest that it can be used in conjunction with GFP to produce an autofluorescent protein capable of presenting random peptides.

Construction of Minibody-GFP Fusion Library

Using methods known in the art (see Example 1), a minibody coding sequence as described in Pessi et al. (1993) is cloned separately into sites located at coding sequences for the N- and C-terminus of GFP in, e.g., pEGFP-C and pEGFP-N (Clontech Catalog 97/98, p. 114–115). These hybrid constructs are tested to ensure that they maintain fluorescence in vivo using a flow sorter or similar device. As described in Martin et al. (1994), cloning sites for a library can be introduced into the modified minibody-GFP vector to permit introduction of random oligonucleotides coding for random 6 amino acid peptides into either one or both of the HVRs in the minibody. After preliminary studies to confirm that the minibody-GFP fusion proteins are autofluorescent, this minibody-GFP scaffold is used to produce a large-scale library as described in Example 1.

EXAMPLE 4

Use of GFP/Peptide Fusions in Genetic Screens/ Selections in Human Cells

The peptide display scaffold of this invention can be used for genetic experiments in mammalian cells, including human cells. Conceptually, these experiments are very similar to those carried out in yeast, but they involve certain technical differences that involve growth of the cells, details of the expression vector used to drive expression of the peptide scaffold, and transfer of DNA into the cells (e.g., PCT US97 145 14, Selection Systems for the Identification of Genes Based on Functional Analysis). For the purposes of the invention described herein, we give a specific example of a mammalian expression vector.

Figure 6:
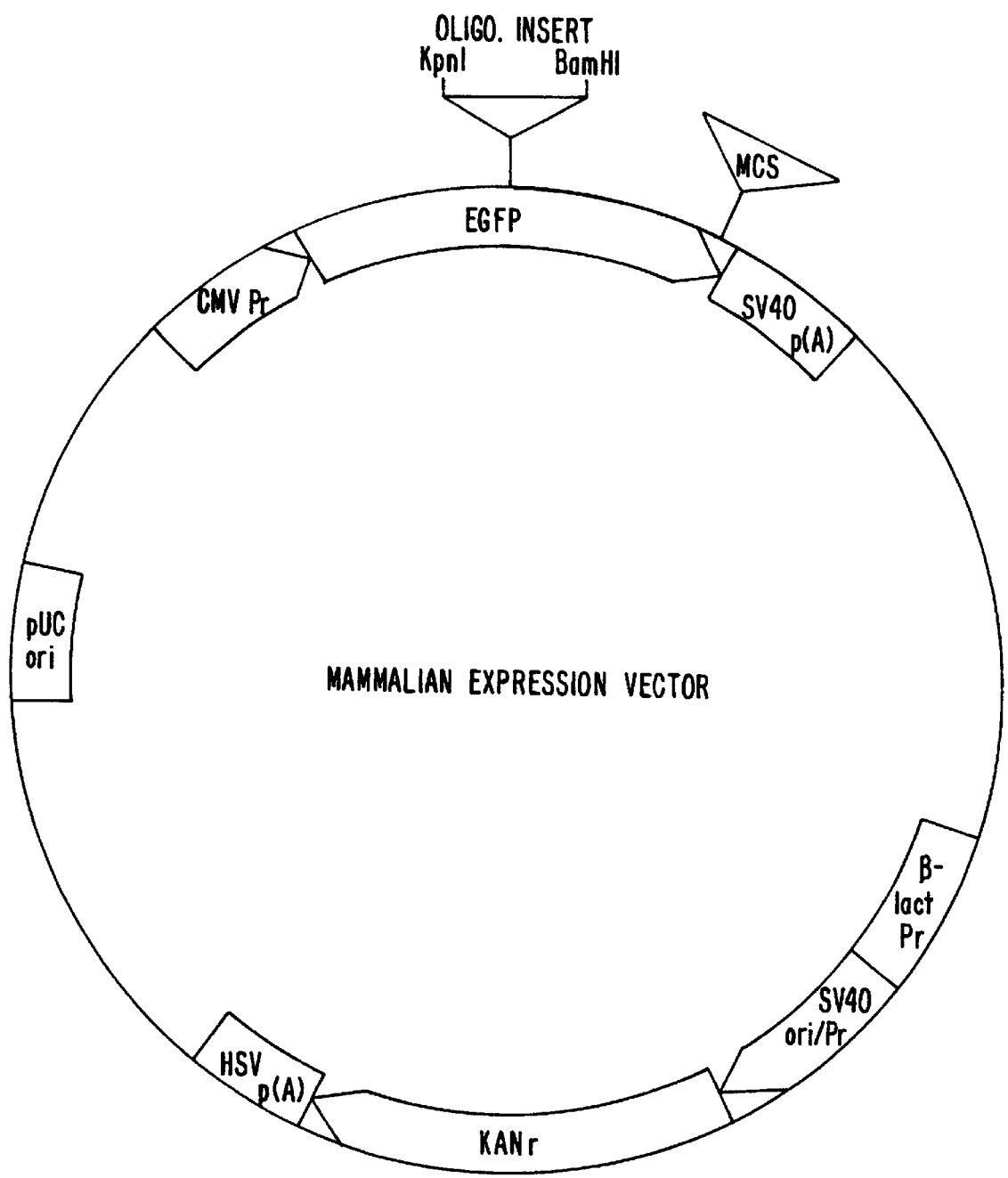
FIG. 6: Map of mammalian expression vector.

The expression library is constructed in the vector shown in FIG. 6. The vector is similar in design to that of FIG. 2. It is based on pEGFP-C1 (Clontech) which contains a pUC 10 origin of replication, and a bacterial promotor upstream of the gene encoding kanamycin resistance; these allow selection and propagation in *E. coli*. The vector also contains signals for selection and maintenance in mammalian cells: an SV40 promotor that drives expression of a neomycin resistance gene followed by an SV40 polyadenylation signal and an SV40 origin of replication. The vector encodes a red-shifted GFP variant optimized for expression in mammalian cells linked to a multiple cloning site and polyadenylation signal. The EGFP sequence was modified as described in Example 1 to contain a KpnI/EcoRI/BamHI linker at codon position 156/157 (as in pVT27, Example 1). The modified EGFP sequence was cloned into the EGFP-C1 vector treated previously to remove the BamHI site in its polylinker (by digestion with BglII and BamHI and religation, thus forming a BglII/BamHI hybrid site in the multiple cloning site). Two "splint" oligonucleotides labeled "antisense" were annealed to the randomer oligonucleotide ("sense") under conditions favoring formation of perfectly matched duplex (as in Example 1), and ligated into the KpnI/BamHI digested vector to generate a large population of in-frame, random 45-mer oligonucleotide insert sequences for expression of random 15-mer peptide insertions in GFP in mammalian cells. The oligonucleotide sequences are:

sense: 5' C. AGC GCT GG-(NNX)15-GGG TCC GCA G 3' antisense: 3' CA TGG TCG CGA CCG 5' 3' CCC AGG CGT CCT AG 5'

The above examples are provided to illustrate the invention but not to limit its scope. Other variants of the invention will be readily apparent to one of ordinary skill in the art and encompassed by the appended claims. All publications, patents, and patent applications cited herein are hereby incorporated by reference.

What is claimed is:

1. A nucleic acid sequence encoding a peptide display scaffold comprising:
    a) a first scaffold sequence encoding a GFP; and
    b) a second sequence encoding a peptide and inserted at a site located in a region of said first scaffold sequence encoding said GFP selected from the group consisting of nucleic acid sequences corresponding to (i) a solvent-exposed region encompassing Thr49-Thr50 of said GFP; (ii) a solvent-exposed region encompassing Met78-Lys79 of said GFP; (iii) a solvent-exposed region encompassing Gly116-Asp 117 of said GFP; (iv)

a solvent-exposed region encompassing Lys140-Leu141 of said GFP; (v) a solvent-exposed region encompassing Gly134-Asn135 of said GFP; (vi) a solvent-exposed region encompassing Gly157-Lys158 of said GFP; (vii) a solvent-exposed region encompassing Glu172-Asp173 of said GFP; (viii) a solvent-exposed region encompassing Leu194-Leu195 of said GFP; (ix) a solvent-exposed region encompassing Gly189-Asp190 of said GFP; and (x) a solvent-exposed region encompassing Glu213-Lys214 of said GFP; wherein said second sequence and said first scaffold sequence encode a second protein capable of emitting light, and wherein said peptide is displayed in a contained conformation in which said peptide is tethered at both ends within said second protein.

2. The nucleic acid sequence of claim 1 wherein the GFP is a green fluorescent protein derived from the jellyfish *Aequorea victoria*.

3. The nucleic acid sequence of claim 2 wherein the GFP is wild type green fluorescent protein from the jellyfish *Aequorea victoria*.

4. The nucleic acid sequence of claim 2, wherein the GFP is EGFP.

5. An expression vector comprising:
   a) a first nucleic acid sequence encoding a GFP; and
   b) a second sequence encoding a peptide and inserted at an insertion site located in a region of said first scaffold sequence encoding GFP selected from the group consisting of nucleic acid sequences corresponding to (i) a solvent-exposed region encompassing Thr49-Thr50 of said GFP; (ii) a solvent-exposed region encompassing Met78-Lys79 of said GFP; (iii) a solvent-exposed region encompassing Gly116-Asp117 of said GFP; (iv) a solvent-exposed region encompassing Lys140-Leu141 of said GFP; (v) a solvent-exposed region encompassing Gly134-Asn135 of said GFP; (vi) a solvent-exposed region encompassing Gly157-Lys158 of said GFP; (vii) a solvent-exposed region encompassing Glu172-Asp173 of said GFP; (viii) a solvent-exposed region encompassing Leu194-leu195 of said GFP; (ix) a solvent-exposed region encompassing Gly189-Asp190 of said GFP; and (x) a solvent-exposed region encompassing Glu213-Lys214 of said GFP;
wherein said second sequence and said first sequence encode a second protein capable of emitting light, and wherein said peptide is displayed in a constrained conformation in which said peptide is tethered at both ends as part of said second protein.

6. The expression vector of claim 5 wherein said GFP is derived from the jellyfish *Aequorea Victoria*.

7. The expression vector of claim 6 wherein the GFP is wild type green fluorescent protein from the jellyfish *Aequorea victoria*.

8. The expression vector of claim 6, wherein the GFP is EGFP.

9. The nucleic acid sequence of claim 1, wherein the site is located in the region of the first sequence encoding the solvent-exposed region encompassing Thr49-Thr50 of said GFP.

10. The nucleic acid sequence of claim 1, wherein the site is located in the region of the first sequence encoding the solvent-exposed region encompassing Met78-Lys79 of said GFP.

11. The nucleic acid sequence of claim 1, wherein the site is located in the region of the first sequence encoding the solvent-exposed region encompassing Gly116-Asp117 of said GFP.

12. The nucleic acid sequence of claim 1, wherein the site is located in the region of the first sequence encoding the solvent-exposed region encompassing Lys140-Leu141 or Gly134-Asn135 of said GFP.

13. The nucleic acid sequence of claim 1, wherein the site is located in the region of the first sequence encoding the solvent-exposed region encompassing Gln157-Lys158 of said GFP.

14. The nucleic acid sequence of claim 1, wherein the site is located in the region of the first sequence encoding the solvent-exposed region encompassing Glu172-Asp173 of said GFP.

15. The nucleic acid sequence of claim 1, wherein the site is located in the region of the first sequence encoding the solvent-exposed region encompassing Leu194-Leu195 or Gly189-Asp190 of said GFP.

16. The nucleic acid sequence of claim 1, wherein the site is located in the region of the first sequence encoding the solvent-exposed region encompassing Glu213-Lys214 of said GFP.

17. A nucleic acid sequence encoding a peptide display scaffold comprising:
   a) a first scaffold sequence encoding a GFP; and
   b) a second sequence encoding a peptide and inserted at a site located in a region of said first scaffold sequence encoding said GFP selected from the group consisting of nucleic acid sequences corresponding to (i) a beta-turn region encompassing Thr49-Thr50 of said GFP; (ii) a beta-turn region encompassing Met78-Lys79 of said GFP; (iii) a beta-turn region encompassing Gly116-Asp117 of said GFP; (iv) a beta-turn region encompassing Lys140-Leu141 of said GFP; (v) a beta-turn region encompassing Gly134-Asn135 of said GFP; (vi) a beta-turn region encompassing Gly157-Lys158 of said GFP; (vii) a beta-turn region encompassing Glu172-Asp173 of said GFP; (viii) a beta-turn region encompassing Leu194-Leu195 of said GFP; (ix) a beta-turn region encompassing Gly189-Asp190 of said GFP; and (x) a beta-turn region encompassing Glu213-Lys214 of said GFP;
wherein said second sequence and said first scaffold sequence encode a second protein capable of emitting light, and wherein said peptide is displayed in a constrained conformation in which said peptide is tethered at both ends within said second protein.

18. The nucleic acid sequence of claim 17, wherein the site is located in the region of the first sequence encoding the beta-turn region encompassing Thr49-Thr50 of said GFP.

19. The nucleic acid sequence of claim 17, wherein the site is located in the region of the it sequence encoding the beta-turn region encompassing Met78-Lys79 of said GFP.

20. The nucleic acid sequence of claim 17, wherein the site is located in the region of the first sequence encoding the beta-turn region encompassing Gly116-Asp117 of said GFP.

21. The nucleic acid sequence of claim 17, wherein the site is located in the region of the first sequence encoding the beta-turn region encompassing Lys140-Leu141 or Gly134-Asn135 of said GFP.

22. The nucleic acid sequence of claim 17, wherein the site is located in the region of the first sequence encoding the beta-turn region encompassing Gln157-Lys158 of said GFP.

23. The nucleic acid sequence of claim 17, wherein the site is located in the region of the first sequence encoding the beta-turn region encompassing Glu172-Asp173 of said GFP.

24. The nucleic acid sequence of claim 17, wherein the site is located in the region of the first sequence encoding the beta-turn region encompassing Leu194-Leu195 or Gly189-Asp190 of said GFP.

25. The nucleic acid sequence of claim 17, wherein the site is located in the region of the first sequence encoding the beta-turn region encompassing Glu213-Lys214 of said GFP.

26. The expression vector of claim 5, wherein the site is located in the region of the first sequence encoding the solvent-exposed region encompassing Thr49-Thr50 of said GFP.

27. The expression vector of claim 5, wherein the site is located in the region of the first sequence encoding the solvent-exposed region encompassing Met78-Lys79 of said GFP.

28. The expression vector of claim 5, wherein the site is located in the region of the first sequence encoding the solvent-exposed region encompassing Gly116-Asp117 of said GFP.

29. The expression vector of claim 5, wherein the site is located in the region of the first sequence encoding the solvent-exposed region encompassing Lys140-Leu141 or Gly134-Asn135 of said GFP.

30. The expression vector of claim 5, wherein the site is located in the region of the first sequence encoding the solvent-exposed region encompassing Gln157-Lys158 of said GFP.

31. The expression vector of claim 5, wherein the site is located in the region of the first sequence encoding the solvent-exposed region encompassing Glu172-Asp173 of said GFP.

32. The expression vector of claim 5, wherein the site is located in the region of the fist sequence encoding the solvent-exposed region encompassing Leu194-Leu195 or Gly189-Asp190 of said GFP.

33. The expression vector of claim 5, wherein the site is located in the region of the first sequence encoding the solvent-exposed region encompassing Glu213-Lys214 of said GFP.

34. An expression vector comprising:
  a) a first nucleic acid sequence encoding a GFP; and
  b) a second sequence encoding a peptide and inserted at an insertion site located in a region of said first scaffold sequence encoding GFP selected from the group consisting of nucleic acid sequences corresponding to
  (i) a beta-turn region encompassing Thr49-Thr50 of said GFP;
  (ii) a beta-turn region encompassing Met78-Lys79 of said GFP;
  (iii) a beta-turn region encompassing Gly116-Asp117 of said GFP;
  (iv) a beta-turn region encompassing Lys140-Leu141 of said GFP;
  (v) a beta-turn region encompassing Gly134-Asn135 of said GFP;
  (vi) a beta-turn region encompassing Gly157-Lys158 of said GFP;
  (vii) a beta-turn region encompassing Glu172-Asp173 of said GFP;
  (viii) a beta-turn region encompassing Leu194-Leu195 of said GFP;
  (ix) a beta-turn region encompassing Gly189-Asp190 of said GFP; and
  (x) a beta-turn region encompassing Glu213-Lys214 of said GFP;

wherein said second sequence and said first sequence encode a second protein capable of emitting light, and wherein said peptide is displayed in a constrained conformation in which said peptide is tethered at both ends as part of said second protein.

35. The expression vector of claim 34, wherein the site is located in the region of the first sequence encoding the beta-turn region encompassing Thr49-Thr50 of said GFP.

36. The expression vector of claim 34, wherein the site is located in the region of the first sequence encoding the beta-turn region encompassing Met78-Lys79 of said GFP.

37. The expression vector of claim 34, wherein the site is located in the region of the first sequence encoding the beta-turn region encompassing Gly116-Asp117 of said GFP.

38. The expression vector of claim 34, wherein the site is located in the region of the first sequence encoding the beta-turn region encompassing Lys140-Leu141 or Gly134-Asn135 of said GFP.

39. The expression vector of claim 34, wherein the site is located in the region of the first sequence encoding the beta-turn region encompassing Gln157-Lys158 of said GFP.

40. The expression vector of claim 34, wherein the site is located in the region of the first sequence encoding the beta-turn region encompassing Glu172-Asp173 of said GFP.

41. The expression vector of claim 34, wherein the site is located in the region of the first sequence encoding the beta-turn region encompassing Leu194-Leu195 or Gly189-Asp190 of said GFP.

42. The expression vector of claim 34, wherein the site is located in the region of the fist sequence encoding the beta-turn region encompassing Glu213-Lys214 of said GFP.

* * * * *